United States Patent
Kwon

(10) Patent No.: US 12,063,609 B2
(45) Date of Patent: Aug. 13, 2024

(54) ELECTRONIC DEVICE FOR SYNCHRONIZING TIME OF DIFFERENT DATA RECORDS AND METHOD THEREOF

(71) Applicant: Samsung Electronics Co., Ltd., Suwon-si (KR)

(72) Inventor: Sungjun Kwon, Suwon-si (KR)

(73) Assignee: Samsung Electronics Co., Ltd., Suwon-si (KR)

( * ) Notice: Subject to any disclaimer, the term of this patent is extended or adjusted under 35 U.S.C. 154(b) by 264 days.

(21) Appl. No.: 17/672,156

(22) Filed: Feb. 15, 2022

(65) Prior Publication Data

US 2022/0248355 A1 Aug. 4, 2022

Related U.S. Application Data

(63) Continuation of application No. PCT/KR2022/001647, filed on Jan. 28, 2022.

(30) Foreign Application Priority Data

Jan. 29, 2021 (KR) .......................... 10-2021-0013538

(51) Int. Cl.
*H04W 56/00* (2009.01)
*A61B 5/00* (2006.01)
(Continued)

(52) U.S. Cl.
CPC ......... *H04W 56/0015* (2013.01); *H04W 4/38* (2018.02); *H04W 24/08* (2013.01); *H04W 56/0035* (2013.01)

(58) Field of Classification Search
CPC ........... H04W 56/001; H04W 56/0015; H04W 56/0035; H04W 4/30; H04W 4/38;
(Continued)

(56) References Cited

U.S. PATENT DOCUMENTS 9,537,956 B1 * 1/2017 Sibenac .............. H04W 56/001
10,165,531 B1 * 12/2018 Behera ................ H04W 56/001
(Continued)

FOREIGN PATENT DOCUMENTS

CN 107714014 A 2/2018
CN 110166952 A 8/2019
(Continued)

OTHER PUBLICATIONS

International Search Report with Written Opinion dated May 13, 2022, issued in International Patent Application No. PCT/KR2022/001647.

(Continued)

*Primary Examiner* — Jenee Holland
(74) *Attorney, Agent, or Firm* — Jefferson IP Law, LLP

(57) ABSTRACT

An electronic device is provided. The electronic device includes a communication module, a memory, and a processor operatively connected to the communication module and the memory, the processor is configured to transmit a synchronization signal for generating a synchronization marker to a first sensor device and a second sensor device, receive and store first sensor data, receive and store second sensor data, select reference data serving as a reference from among the first sensor data and the second sensor data, detect the synchronization marker, calculate a required time between synchronization markers of the reference data based on stored sampling information of the reference data and positions of the synchronization marker included in the reference data, and correct and store sampling information of the remaining sensor data other than the reference data.

20 Claims, 7 Drawing Sheets

(51) Int. Cl.
*A61B 5/0205* (2006.01)
*A61B 5/024* (2006.01)
*A61B 5/346* (2021.01)
*H04W 4/38* (2018.01)
*H04W 24/08* (2009.01)
*H04W 24/10* (2009.01)

(58) Field of Classification Search
CPC ...... H04W 24/08; H04W 16/18; H04L 43/00; H04L 41/145
See application file for complete search history.

(56) References Cited

U.S. PATENT DOCUMENTS

| | | | |
|---|---|---|---|
| 10,849,084 B1* | 11/2020 | Al-Shaikhi | H04W 56/001 |
| 2006/0269028 A1* | 11/2006 | Bley | H04W 56/001 375/354 |
| 2008/0049013 A1* | 2/2008 | Nasle | H02J 13/00001 345/419 |
| 2008/0085721 A1* | 4/2008 | Hirano | H04W 16/14 455/452.1 |
| 2008/0194975 A1 | 8/2008 | MacQuarrie et al. | |
| 2009/0318785 A1 | 12/2009 | Ishikawa et al. | |
| 2011/0216660 A1* | 9/2011 | Lee | H04J 3/06 370/252 |
| 2011/0295102 A1* | 12/2011 | Lakkis | A61B 5/02028 600/407 |
| 2012/0263082 A1 | 10/2012 | Garudadri et al. | |
| 2014/0105054 A1* | 4/2014 | Sægrov | H04W 64/00 370/252 |
| 2014/0226648 A1* | 8/2014 | Xing | H04W 56/001 370/350 |
| 2016/0036544 A1 | 2/2016 | Katayama et al. | |
| 2016/0135136 A1* | 5/2016 | Wang | H04W 56/001 370/336 |
| 2016/0183205 A1* | 6/2016 | Li | H04W 56/001 370/350 |
| 2016/0216362 A1* | 7/2016 | Subramanian | G01S 5/10 |
| 2016/0269913 A1* | 9/2016 | Paulraj | H04W 16/18 |
| 2016/0316443 A1* | 10/2016 | Otomo | H04W 52/0219 |
| 2016/0373617 A1 | 12/2016 | Choi | |
| 2017/0000350 A1 | 1/2017 | Kwon et al. | |
| 2017/0095168 A1 | 4/2017 | Kwon et al. | |
| 2018/0041329 A1* | 2/2018 | Wang | H04W 56/0035 |
| 2018/0198545 A1* | 7/2018 | Aichriedler | H04Q 9/04 |
| 2019/0014549 A1* | 1/2019 | Kwan | H04W 56/004 |
| 2019/0037336 A1* | 1/2019 | Yang | H04W 56/0035 |
| 2019/0150106 A1* | 5/2019 | Teruhi | G04R 20/02 370/338 |
| 2019/0208483 A1* | 7/2019 | Luecke | H04W 56/002 |
| 2019/0286857 A1 | 9/2019 | Kataoka et al. | |
| 2019/0296846 A1 | 9/2019 | Aichriedler | |
| 2019/0327697 A1* | 10/2019 | Yau | H04L 7/0012 |
| 2020/0236494 A1* | 7/2020 | Ronan | B60R 25/24 |
| 2020/0259896 A1* | 8/2020 | Sachs | H04W 12/06 |
| 2020/0275394 A1* | 8/2020 | Lam | H04W 76/40 |
| 2020/0400438 A1* | 12/2020 | Fujii | G08G 1/0133 |
| 2021/0000419 A1 | 1/2021 | Gil et al. | |

FOREIGN PATENT DOCUMENTS

| | | |
|---|---|---|
| CN | 111787606 A | 10/2020 |
| JP | 2010-000283 A | 1/2010 |
| JP | 2014-178952 A | 9/2014 |
| JP | 2019-159951 A | 9/2019 |
| KR | 10-1515372 B1 | 4/2015 |
| KR | 10-2017-0004607 A | 1/2017 |
| KR | 10-2017-0040034 A | 4/2017 |
| KR | 10-2018-0045118 A | 5/2018 |
| WO | 2008/095318 A1 | 8/2008 |

OTHER PUBLICATIONS

Extended European Search Report dated May 10, 2024, issued in European Patent Application No. 22746304.9.

* cited by examiner

ELECTRONIC DEVICE FOR SYNCHRONIZING TIME OF DIFFERENT DATA RECORDS AND METHOD THEREOF

CROSS-REFERENCE TO RELATED APPLICATION(S)

This application is a continuation application, claiming priority under § 365(c), of an International application No. PCT/KR2022/001647, filed on Jan. 28, 2022, which is based on and claims the benefit of a Korean patent application number 10-2021-0013538, filed on Jan. 29, 2021, in the Korean Intellectual Property Office, the disclosure of which is incorporated by reference herein in its entirety.

TECHNICAL FIELD

The disclosure relates to an electronic device for synchronizing the time between different pieces of received or acquired data.

BACKGROUND ART

In line with increasing demands for health management, electronic devices use sensors for measuring various biometric signals. Typically used sensors include a pulse sensor/heart rate sensor, an electrocardiogram (ECG) sensor, and a photoplethysmography (PPG) sensor. An electronic device may include the above-mentioned sensors, and the user may use the electronic device to identify biometric signals continuously measured by the sensors.

In line with attention to expandability of sensor technologies and growth of digital data processing technologies, sensor signal collection is typically done by digital signal collecting systems, and high-speed collection is required in most cases to increase the resolution of information.

The above information is presented as background information only to assist with an understanding of the disclosure. No determination has been made, and no assertion is made, as to whether any of the above might be applicable as prior art with regard to the disclosure.

DISCLOSURE OF INVENTION

Technical Problem

In connection with digital signal collection, two or more digital signal collecting systems and be employed to simultaneously collect signals for the purpose of accurate signal measurement or safe signal collection. In the case of biometric signal collection, different digital biometric signal measurement systems may be used to simultaneously collect various biometric signals such as ECG, PPG, movements, body temperature, and the like. In connection with analysis of data collected simultaneously as such, time synchronization between pieces of collected data may be required. For example, in order to observe a change in PPG signal when the ECG signal shows an abnormal symptom, it is necessary to be able to check the PPG signal time-synchronized with the ECG signal at the abnormal point in time. There is a need for a function capable of synchronizing the starting point of a signal (for example, slate) between pieces of digital data requiring time synchronization.

Digital signal collecting systems commonly provide various sampling frequencies such as 25 Hz, 100 Hz, 256 Hz, and 500 Hz in connection with signal collection. However, such sampling frequencies may have errors depending on system design and implementation. Even if the stating points of signals are synchronized between pieces of digital data, the errors may result in gradually increasing time differences between signals over time. Therefore, if continuous signal collection is necessary for a long period of time, there may be a need to perform synchronization at the start and end or, if necessary, periodically, instead of time synchronization at the start only.

Aspects of the disclosure are to address at least the above-mentioned problems and/or disadvantages and to provide at least the advantages described below. Accordingly, an aspect of the disclosure is to provide an electronic device for synchronizing the time between different pieces of received or acquired data.

Additional aspects will be set forth in part in the description which follows and, in part, will be apparent from the description, or may be learned by practice of the presented embodiments.

Solution to Problem

In accordance with an aspect of the disclosure, an electronic device is provided. The electronic device includes a communication module for communicatively establishing a connection with a first sensor device and a second sensor device, a memory for storing first sampling information including at least one of information on a sampling period and information on a sampling frequency of the first sensor device and second sampling information including at least one of information on a sampling period and information on a sampling frequency of the second sensor device, and a processor operatively connected to the communication module and the memory, wherein the processor is configured to transmit a synchronization signal for generating a synchronization marker to the first sensor device and the second sensor device according to a predetermined time interval, receive and store first sensor data including the synchronization marker from the first sensor device, receive and store second sensor data including the synchronization marker from the second sensor device, select reference data serving as a reference from among the first sensor data and the second sensor data, detect the synchronization marker from the first sensor data and the second sensor data, calculate a required time between the synchronization markers of the reference data based on the stored sampling information of the reference data and the position of the synchronization marker included in the detected reference data, and correct and store sampling information of the remaining sensor data other than the reference data based on the required time and the synchronization marker positions of the remaining sensor data other than the reference data.

In accordance with another aspect of the disclosure, a method of correcting sampling information of sensor data received from a plurality of sensor devices by an electronic device is provided. The method includes simultaneously transmitting a synchronization signal for generating a synchronization marker to the first sensor device and the second sensor device connected to the electronic device at least two times based on a predetermined time interval, receiving and storing first sensor data including the synchronization marker from the first sensor device, receiving and storing second sensor data including the synchronization marker from the second sensor device, selecting reference data serving as a reference from among the first sensor data and the second sensor data, detecting the synchronization marker from the first sensor data and the second sensor data, calculating a required time between the synchronization markers of the reference data based on the sampling information of the reference data and the positions of the synchronization markers included in the detected reference data, and correcting and storing sampling information of the remaining sensor data other than the reference data based on the required time and the position of the synchronization marker of the remaining sensor data other than the reference data.

Advantageous Effects of Invention

According to various embodiments, digital signals generated by two or more different electronic devices may be collected, and time synchronization between pieces of the collected data may be performed. Therefore, accuracy of comparative analysis of simultaneously collected data may be improved, and system efficiency and stability may be expected.

Other aspects, advantages, and salient features of the disclosure will become apparent to those skilled in the art from the following detailed description, which, taken in conjunction with the annexed drawings, discloses various embodiments of the disclosure.

BRIEF DESCRIPTION OF DRAWINGS

The above and other aspects, features, and advantages of certain embodiments of the disclosure will be more apparent from the following description taken in conjunction with the accompanying drawings, in which.

Throughout the drawings, it should be noted that like reference numbers are used to depict the same or similar elements, features, and structures.

MODE FOR THE INVENTION

The following description with reference to the accompanying drawings is provided to assist in a comprehensive understanding of various embodiments of the disclosure as defined by the claims and their equivalents. It includes various specific details to assist in that understanding but these are to be regarded as merely exemplary. Accordingly, those of ordinary skill in the art will recognize that various changes and modifications of the various embodiments described herein can be made without departing from the scope and spirit of the disclosure. In addition, descriptions of well-known functions and constructions may be omitted for clarity and conciseness.

The terms and words used in the following description and claims are not limited to the bibliographical meanings, but, are merely used by the inventor to enable a clear and consistent understanding of the disclosure. Accordingly, it should be apparent to those skilled in the art that the following description of various embodiments of the disclosure is provided for illustration purpose only and not for the purpose of limiting the disclosure as defined by the appended claims and their equivalents.

It is to be understood that the singular forms "a," "an," and "the" include plural referents unless the context clearly dictates otherwise. Thus, for example, reference to "a component surface" includes reference to one or more of such surfaces.

Figure 1:
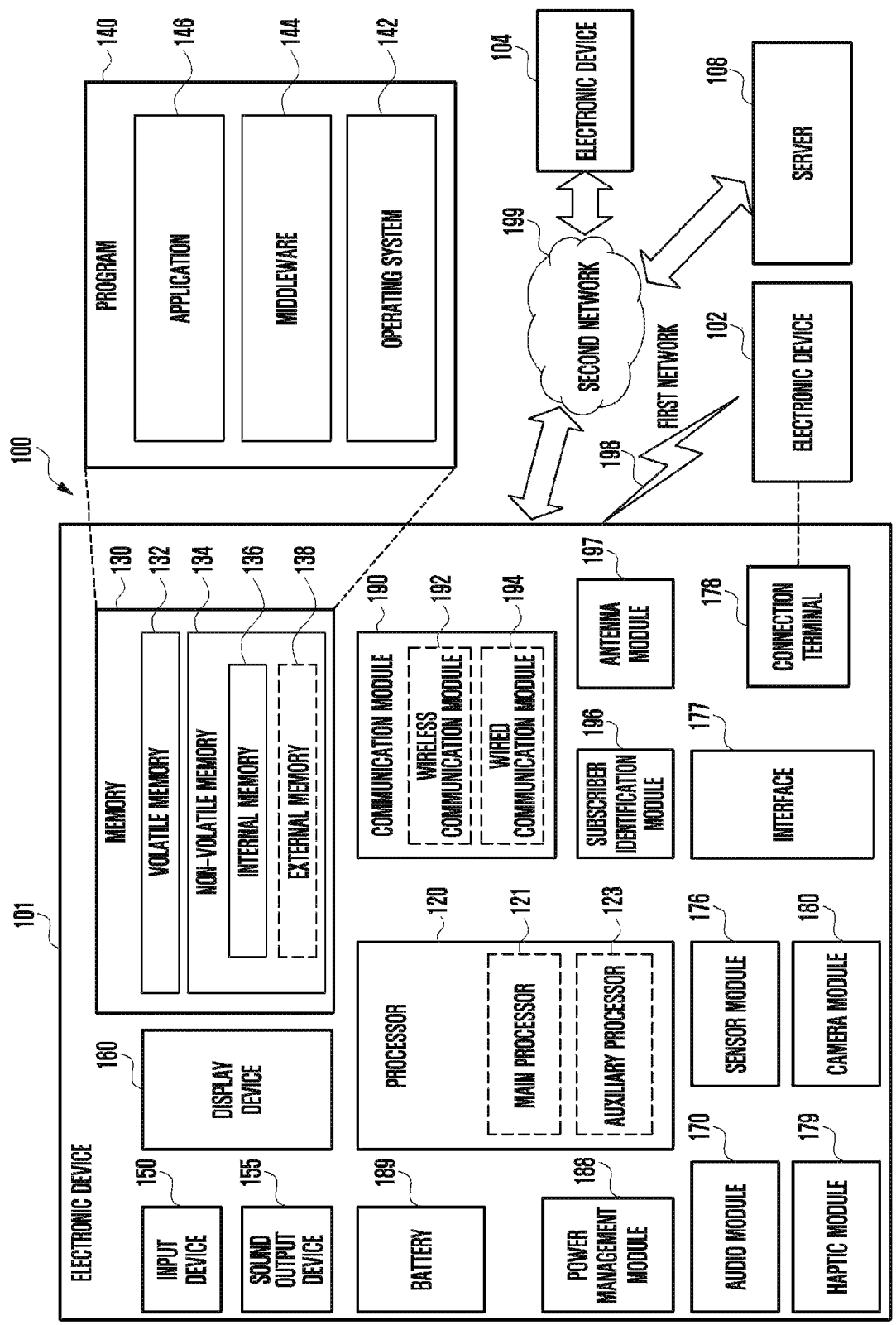
FIG. 1 is a block diagram illustrating an electronic device in a network environment according to an embodiment of the disclosure.

FIG. 1 is a block diagram illustrating an electronic device in a network environment according to an embodiment of the disclosure.

Referring to FIG. 1, an electronic device 101 in a network environment 100 may communicate with an external electronic device 102 via a first network 198 (e.g., a short-range wireless communication network), or at least one of an external electronic device 104 or a server 108 via a second network 199 (e.g., a long-range wireless communication network). According to an embodiment, the electronic device 101 may communicate with the external electronic device 104 via the server 108. According to an embodiment, the electronic device 101 may include a processor 120, a memory 130, an input device 150, a sound output device 155, a display device 160, an audio module 170, a sensor module 176, an interface 177, a connection terminal 178, a haptic module 179, a camera module 180, a power management module 188, a battery 189, a communication module 190, a subscriber identification module (SIM) 196, or an antenna module 197. In some embodiments, at least one of the components (e.g., the connection terminal 178) may be omitted from the electronic device 101, or one or more other components may be added in the electronic device 101. In some embodiments, some of the components (e.g., the sensor module 176, the camera module 180, or the antenna module 197) may be implemented as a single component (e.g., the display device 160).

The processor 120 may execute, for example, software (e.g., a program 140) to control at least one other component (e.g., a hardware or software component) of the electronic device 101 coupled with the processor 120, and may perform various data processing or computation. According to one embodiment, as at least part of the data processing or computation, the processor 120 may store a command or data received from another component (e.g., the sensor module 176 or the communication module 190) in a volatile memory 132, process the command or the data stored in the volatile memory 132, and store resulting data in a non-volatile memory 134. According to an embodiment, the processor 120 may include a main processor 121 (e.g., a central processing unit (CPU) or an application processor (AP)), or an auxiliary processor 123 (e.g., a graphics processing unit (GPU), a neural processing unit (NPU), an image signal processor (ISP), a sensor hub processor, or a communication processor (CP)) that is operable independently from, or in conjunction with, the main processor 121. For example, when the electronic device 101 includes the main processor 121 and the auxiliary processor 123, the auxiliary processor 123 may be adapted to consume less power than the main processor 121, or to be specific to a specified function. The auxiliary processor 123 may be implemented as separate from, or as part of the main processor 121.

The auxiliary processor 123 may control at least some of functions or states related to at least one component (e.g., the display device 160, the sensor module 176, or the communication module 190) among the components of the electronic device 101, instead of the main processor 121 while the main processor 121 is in an inactive (e.g., sleep) state, or together with the main processor 121 while the main processor 121 is in an active state (e.g., executing an application). According to an embodiment, the auxiliary processor 123 (e.g., an image signal processor or a communication processor) may be implemented as part of another component (e.g., the camera module 180 or the communication module 190) functionally related to the auxiliary processor 123. According to an embodiment, the auxiliary processor 123 (e.g., the neural processing unit) may include a hardware structure specified for artificial intelligence model processing. An artificial intelligence model may be generated by machine learning. Such learning may be performed, e.g., by the electronic device 101 where the artificial intelligence is performed or via a separate server (e.g., the server 108). Learning algorithms may include, but are not limited to, e.g., supervised learning, unsupervised learning, semi-supervised learning, or reinforcement learning. The artificial intelligence model may include a plurality of artificial neural network layers. The artificial neural network may be a deep neural network (DNN), a convolutional neural network (CNN), a recurrent neural network (RNN), a restricted boltzmann machine (RBM), a deep belief network (DBN), a bidirectional recurrent deep neural network (BRDNN), deep Q-network or a combination of two or more thereof but is not limited thereto. The artificial intelligence model may, additionally or alternatively, include a software structure other than the hardware structure.

The memory 130 may store various data used by at least one component (e.g., the processor 120 or the sensor module 176) of the electronic device 101. The various data may include, for example, software (e.g., the program 140) and input data or output data for a command related thereto. The memory 130 may include the volatile memory 132 or the non-volatile memory 134.

The program 140 may be stored in the memory 130 as software, and may include, for example, an operating system (OS) 142, middleware 144, or an application 146.

The input device 150 may receive a command or data to be used by another component (e.g., the processor 120) of the electronic device 101, from the outside (e.g., a user) of the electronic device 101. The input device 150 may include, for example, a microphone, a mouse, a keyboard, a key (e.g., a button), or a digital pen (e.g., a stylus pen).

The sound output device 155 may output sound signals to the outside of the electronic device 101. The sound output device 155 may include, for example, a speaker or a receiver. The speaker may be used for general purposes, such as playing multimedia or playing record. The receiver may be used for receiving incoming calls. According to an embodiment, the receiver may be implemented as separate from, or as part of the speaker.

The display device 160 may visually provide information to the outside (e.g., a user) of the electronic device 101. The display device 160 may include, for example, a display, a hologram device, or a projector and control circuitry to control a corresponding one of the display, hologram device, and projector. According to an embodiment, the display device 160 may include a touch sensor adapted to detect a touch, or a pressure sensor adapted to measure the intensity of force incurred by the touch.

The audio module 170 may convert a sound into an electrical signal and vice versa. According to an embodiment, the audio module 170 may obtain the sound via the input device 150, or output the sound via the sound output device 155 or a headphone of an external electronic device (e.g., the external electronic device 102) directly (e.g., wiredly) or wirelessly coupled with the electronic device 101.

The sensor module 176 may detect an operational state (e.g., power or temperature) of the electronic device 101 or an environmental state (e.g., a state of a user) external to the electronic device 101, and then generate an electrical signal or data value corresponding to the detected state. According to an embodiment, the sensor module 176 may include, for example, a gesture sensor, a gyro sensor, an atmospheric pressure sensor, a magnetic sensor, an acceleration sensor, a grip sensor, a proximity sensor, a color sensor, an infrared (IR) sensor, a biometric sensor, a temperature sensor, a humidity sensor, or an illuminance sensor.

The interface 177 may support one or more specified protocols to be used for the electronic device 101 to be coupled with the external electronic device (e.g., the external electronic device 102) directly (e.g., wiredly) or wirelessly. According to an embodiment, the interface 177 may include, for example, a high definition multimedia interface (HDMI), a universal serial bus (USB) interface, a secure digital (SD) card interface, or an audio interface.

The connection terminal 178 may include a connector via which the electronic device 101 may be physically connected with the external electronic device (e.g., the external electronic device 102). According to an embodiment, the connection terminal 178 may include, for example, a HDMI connector, a USB connector, a SD card connector, or an audio connector (e.g., a headphone connector).

The haptic module 179 may convert an electrical signal into a mechanical stimulus (e.g., a vibration or a movement) or electrical stimulus which may be recognized by a user via his tactile sensation or kinesthetic sensation. According to an embodiment, the haptic module 179 may include, for example, a motor, a piezoelectric element, or an electric stimulator.

The camera module 180 may capture a still image or moving images. According to an embodiment, the camera module 180 may include one or more lenses, image sensors, image signal processors, or flashes.

The power management module 188 may manage power supplied to the electronic device 101. According to one embodiment, the power management module 188 may be implemented as at least part of, for example, a power management integrated circuit (PMIC).

The battery 189 may supply power to at least one component of the electronic device 101. According to an embodiment, the battery 189 may include, for example, a primary cell which is not rechargeable, a secondary cell which is rechargeable, or a fuel cell.

The communication module 190 may support establishing a direct (e.g., wired) communication channel or a wireless communication channel between the electronic device 101 and the external electronic device (e.g., the external electronic device 102, the external electronic device 104, or the server 108) and performing communication via the established communication channel. The communication module 190 may include one or more communication processors that are operable independently from the processor 120 (e.g., the application processor (AP)) and supports a direct (e.g., wired) communication or a wireless communication. According to an embodiment, the communication module 190 may include a wireless communication module 192 (e.g., a cellular communication module, a short-range wireless communication module, or a global navigation satellite system (GNSS) communication module) or a wired communication module 194 (e.g., a local area network (LAN) communication module or a power line communication (PLC) module). A corresponding one of these communication modules may communicate with the external electronic device via the first network 198 (e.g., a short-range communication network, such as Bluetooth™, wireless-fidelity (Wi-Fi) direct, or infrared data association (IrDA)) or the second network 199 (e.g., a long-range communication network, such as a legacy cellular network, a fifth generation (5G) network, a next-generation communication network, the Internet, or a computer network (e.g., LAN or wide area network (WAN)). These various types of communication modules may be implemented as a single component (e.g., a single chip), or may be implemented as multi components (e.g., multi chips) separate from each other. The wireless communication module 192 may identify and authenticate the electronic device 101 in a communication network, such as the first network 198 or the second network 199, using subscriber information (e.g., international mobile subscriber identity (IMSI)) stored in the subscriber identification module 196.

The wireless communication module 192 may support a 5G network, after a fourth generation (4G) network, and next-generation communication technology, e.g., new radio (NR) access technology. The NR access technology may support enhanced mobile broadband (eMBB), massive machine type communications (mMTC), or ultra-reliable and low-latency communications (URLLC). The wireless communication module 192 may support a high-frequency band (e.g., the mmWave band) to achieve, e.g., a high data transmission rate. The wireless communication module 192 may support various technologies for securing performance on a high-frequency band, such as, e.g., beamforming, massive multiple-input and multiple-output (massive MIMO), full dimensional MIMO (FD-MIMO), array antenna, analog beam-forming, or large scale antenna. The wireless communication module 192 may support various requirements specified in the electronic device 101, an external electronic device (e.g., the external electronic device 104), or a network system (e.g., the second network 199). According to an embodiment, the wireless communication module 192 may support a peak data rate (e.g., 20 Gbps or more) for implementing eMBB, loss coverage (e.g., 164 dB or less) for implementing mMTC, or U-plane latency (e.g., 0.5 ms or less for each of downlink (DL) and uplink (UL), or a round trip of 1 ms or less) for implementing URLLC.

The antenna module 197 may transmit or receive a signal or power to or from the outside (e.g., the external electronic device) of the electronic device 101. According to an embodiment, the antenna module 197 may include an antenna including a radiating element composed of a conductive material or a conductive pattern formed in or on a substrate (e.g., a printed circuit board (PCB)). According to an embodiment, the antenna module 197 may include a plurality of antennas (e.g., array antennas). In such a case, at least one antenna appropriate for a communication scheme used in the communication network, such as the first network 198 or the second network 199, may be selected, for example, by the communication module 190 (e.g., the wireless communication module 192) from the plurality of antennas. The signal or the power may then be transmitted or received between the communication module 190 and the external electronic device via the selected at least one antenna. According to an embodiment, another component (e.g., a radio frequency integrated circuit (RFIC)) other than the radiating element may be additionally formed as part of the antenna module 197.

According to various embodiments, the antenna module 197 may form an mmWave antenna module. According to an embodiment, the mmWave antenna module may include a printed circuit board, a RFIC disposed on a first surface (e.g., the bottom surface) of the printed circuit board, or adjacent to the first surface and capable of supporting a designated high-frequency band (e.g., the mmWave band), and a plurality of antennas (e.g., array antennas) disposed on a second surface (e.g., the top or a side surface) of the printed circuit board, or adjacent to the second surface and capable of transmitting or receiving signals of the designated high-frequency band.

At least some of the above-described components may be coupled mutually and communicate signals (e.g., commands or data) therebetween via an inter-peripheral communication scheme (e.g., a bus, general purpose input and output (GPIO), serial peripheral interface (SPI), or mobile industry processor interface (MIPI)).

According to an embodiment, commands or data may be transmitted or received between the electronic device 101 and the external electronic device 104 via the server 108 coupled with the second network 199. Each of the external electronic devices 102 or 104 may be a device of a same type as, or a different type, from the electronic device 101. According to an embodiment, all or some of operations to be executed at the electronic device 101 may be executed at one or more of the external electronic devices 102 and 104 or the server 108. For example, if the electronic device 101 should perform a function or a service automatically, or in response to a request from a user or another device, the electronic device 101, instead of, or in addition to, executing the function or the service, may request the one or more external electronic devices to perform at least part of the function or the service. The one or more external electronic devices receiving the request may perform the at least part of the function or the service requested, or an additional function or an additional service related to the request, and transfer an outcome of the performing to the electronic device 101. The electronic device 101 may provide the outcome, with or without further processing of the outcome, as at least part of a reply to the request. To that end, a cloud computing, distributed computing, mobile edge computing (MEC), or client-server computing technology may be used, for example. The electronic device 101 may provide ultra low-latency services using, e.g., distributed computing or mobile edge computing. In another embodiment, the external electronic device 104 may include an internet-of-things (IoT) device. The server 108 may be an intelligent server using machine learning and/or a neural network. According to an embodiment, the external electronic device 104 or the server 108 may be included in the second network 199. The electronic device 101 may be applied to intelligent services (e.g., smart home, smart city, smart car, or healthcare) based on 5G communication technology or IoT-related technology.

Figure 2:
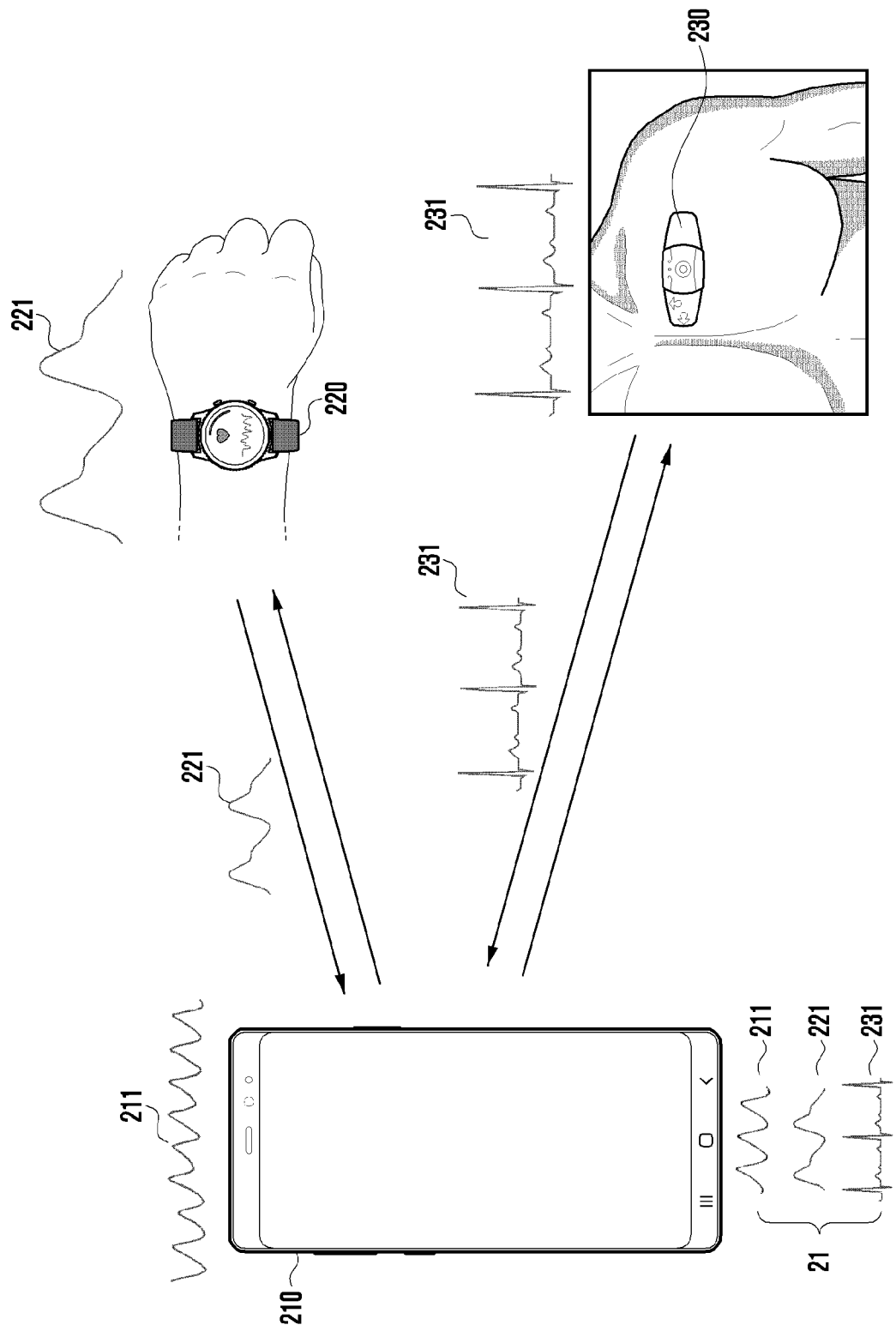
FIG. 2 is an example in which an electronic device transmits/receives data to and from a plurality of external electronic devices according to an embodiment of the disclosure.

FIG. 2 is an example in which an electronic device transmits/receives data to and from a plurality of external electronic devices according to an embodiment of the disclosure.

Referring to FIG. 2, an electronic device 210 may be connected to a plurality of external electronic devices (e.g., a first external electronic device 220 and a second external electronic device 230).

According to various embodiments, the electronic device 210 may include a communication module (e.g., communication module 310 of FIG. 3) and communicate with the first external electronic device 220 and/or the second external electronic device 230 through a wireless communication network (e.g., the first network 198 and/or the second network 199 of FIG. 1). According to various embodiments, the electronic device 210 may transmit/receive data to and from the first external electronic device 220 and/or the second external electronic device 230 using a wireless communication network. According to various embodiments, the electronic device 210 may receive various data including sensor data (e.g., first sensor data 221) measured by the first external electronic device 220 from the first external electronic device 220. According to various embodiments, the electronic device 210 may receive various data including sensor data (e.g., second sensor data 231) measured by the second external electronic device 230 from the second external electronic device 230. According to an embodiment, the electronic device 210 may transmit necessary data to the first external electronic device 220 and the second external electronic device 230 simultaneously or separately. The data that the electronic device 210 can transmit to the plurality of external electronic devices (e.g., first external electronic device 220 and/or second external electronic device 230) may be data for controlling the first external electronic device 220 and/or the second external electronic device 230, or data required for communication with the first external electronic device 220 and/or the second external electronic device 230. According to an embodiment, the electronic device 210 may transmit a signal (e.g., synchronization signal) for generating data (e.g., synchronization marker) including a predetermined format to the first external electronic device 220 and/or the second external electronic device 230.

According to various embodiments, at least one external electronic device (e.g., the first external electronic device 220 and/or the second external electronic device 230) may be communicatively connected to the electronic device 210. Although the number of external electronic devices (e.g., the first external electronic device 220 and/or the second external electronic device 230) is not limited, in this disclosure, for convenience, only two external electronic devices (e.g., the first external electronic device 220 and the second external electronic device 230) will be described. According to various embodiments, each of the first external electronic device 220 and the second external electronic device 230 may include at least one sensor (not illustrated), and may generate sensor data by using a signal measured by each of the sensors. The first external electronic device 220 and/or the second external electronic device 230 may be an electronic device that includes a sensor (not illustrated) such as a smartwatch or an electrocardiogram, and a communication module (not illustrated) for wireless network communication. According to various embodiments, the sensor included in each of the first external electronic device 220 and the second external electronic device 230 may continuously generate an analog electrical signal while driving, and the first external electronic device 220 and/or the second external electronic device 230 may digitize the generated analog electrical signal by sampling according to a predetermined sampling period. The sensor data generated by the first external electronic device 220 and/or the second external electronic device 230 may be digital data sampled at regular intervals. According to various embodiments, the first external electronic device 220 and/or the second external electronic device 230 may each have different sampling cycles. According to an embodiment, the first external electronic device 220 may generate the digitized first sensor data 221 according to the first sampling period. According to an embodiment, the second external electronic device 230 may generate the digitized second sensor data 231 according to the second sampling period. According to an embodiment, the first external electronic device 220 and/or the second external electronic device 230 may include a plurality of sensors (not illustrated), and may sample sensor data according to different sampling periods for each of the plurality of sensors. According to various embodiments, the first external electronic device 220 and/or the second external electronic device 230 may receive a signal transmitted by the electronic device 210 and generate predetermined data (e.g., synchronization marker) based on the received signal. According to various embodiments, the first external electronic device 220 and/or the second external electronic device 230 may transmit the generated sensor data (e.g., first sensor data 221 and/or second sensor data 231) to the electronic device 210. According to an embodiment, the first external electronic device 220 may include predetermined data (e.g., synchronization marker) generated according to a signal (e.g., synchronization signal) received from the electronic device 210 in the generated sensor data (e.g., first sensor data 221), and may transmit the first sensor data 221 including the synchronization marker to the electronic device 210. According to an embodiment, the second external electronic device 230 may include predetermined data (e.g., synchronization marker) generated according to a signal (e.g., synchronization signal) received from the electronic device 210 in the generated sensor data (e.g., second sensor data 231), and may transmit the second sensor data 231 including the synchronization marker to the electronic device 210.

According to various embodiments, the electronic device 210 may receive sensor data (e.g., first sensor data 221 and/or second sensor data 231) generated and transmitted by each external electronic device (e.g., first external electronic device 220 and second external electronic device 230) from the first external electronic device 220 and the second external electronic device 230. According to an embodiment, the sensor data (e.g., first sensor data 221 and/or second sensor data 231) received by the electronic device 210 may include data (e.g., synchronization marker) generated by the first external electronic device 220 and/or the second external electronic device 230 based on a signal (e.g., synchronization signal) transmitted by the electronic device 210.

According to various embodiments, the electronic device 210 may include a sensor (e.g., sensor module 320 of FIG. 3) and measure sensor data. According to an embodiment, the electronic device 210 may receive sensor data (e.g., first sensor data 221 and/or second sensor data 231) from at least one external electronic device (e.g., the first external electronic device 220 and/or the second external electronic device 230) and simultaneously generate sensor data (e.g., third sensor data 211) using the sensor module 320. According to various embodiments, sensors included in each electronic device may continuously measure an analog electrical signal while driving, and the electronic device 210 may digitize the generated analog electrical signal by sampling according to a predetermined sampling period. The sensor data (e.g., the third sensor data 211) generated by the electronic device 210 may be digital data sampled at regular intervals. According to various embodiments, the electronic device 210 may have a constant sampling period.

According to an embodiment, the first external electronic device 220 may generate the digitized third sensor data 211 according to the third sampling period. According to an embodiment, the electronic device 210 may include a plurality of sensors (e.g., the sensor module 320 of FIG. 3), and may sample sensor data according to different sampling periods for each of the plurality of sensors.

According to various embodiments, the electronic device 210 may compare and analyze directly generated sensor data (e.g., the third sensor data 211) and sensor data (e.g., first sensor data 221 and/or second sensor data 231) received from an external electronic device (e.g., the first external electronic device 220 and/or the second external electronic device 230). According to an embodiment, the electronic device 210 may check sampling information related to sampling of sensor data generated by each of the external electronic devices (e.g., first external electronic device 220 and second external electronic device 230) and may store the sampling information in advance in a memory (e.g., memory 330 in FIG. 3). The sampling information may store, for example, at least one of sampling period information about a sampling period in which the external electronic device (e.g., the first external electronic device 220 and/or the second external electronic device 230 of FIG. 2) samples sensor data, sampling frequency information about a sampling frequency, and count (section size value) information. The count information may be, for example, a value of a section size of a memory allocated to each sensor data or a value storing the number of sampled sample data. According to an embodiment, the electronic device 210 may store predetermined sampling information for each external electronic device (e.g., first external electronic device 220 and second external electronic device 230). The electronic device 210 may analyze obtained sensor data 21 using sampling information stored in the memory 330. In the synchronization method disclosed in the disclosure, examples of available sampling information are not limited, but hereinafter, for convenience, a sampling period will be mainly described. The description of the sampling period or the sampling period information disclosed in the disclosure may be substituted with the description of the sampling frequency or the sampling frequency information, or may be substituted with the description of the count or the count information. According to an embodiment, the electronic device 210 may store sampling period information (e.g., first sampling period information and second sampling period information), which is information about a sampling period of sensor data generated by each external electronic device (e.g., first external electronic device 220 and second external electronic device 230), in advance in a memory (e.g., the memory 330 of FIG. 3), and may store sampling period information (e.g., the third sampling period information) of a sensor (e.g., the sensor module 320 of FIG. 3) of the electronic device 210. The electronic device 210 may check the stored sampling period information and perform analysis using the sampling period information and the obtained sensor data 21.

According to various embodiments, the electronic device may synchronize the received and generated sensor data 21 with each other. According to an embodiment, in order for the electronic device 210 to analyze the obtained sensor data 21, it may be necessary for a plurality of sensor data (e.g., first sensor data 221, second sensor data 231 and/or third sensor data 211) to be synchronized with each other. For example, in order to compare different sensor data for an event occurring at a specific time, there may be a need for a plurality of sensor data (e.g., first sensor data 221, second sensor data 231 and/or third sensor data 211) to be aligned on the same time axis. According to an embodiment, the electronic device 210 may synchronize the plurality of sensor data 21 by measuring the sampling period information (e.g.: first sampling period information, second sampling period information, and/or third sampling period information) stored in the memory 330 for the plurality of sensor data (e.g., first sensor data 221, second sensor data 231 and/or third sensor data 211), calculating or correcting an error between the sampling period information and the actual sampling period, and updating the sampling period information in which the error is corrected.

Figure 3:
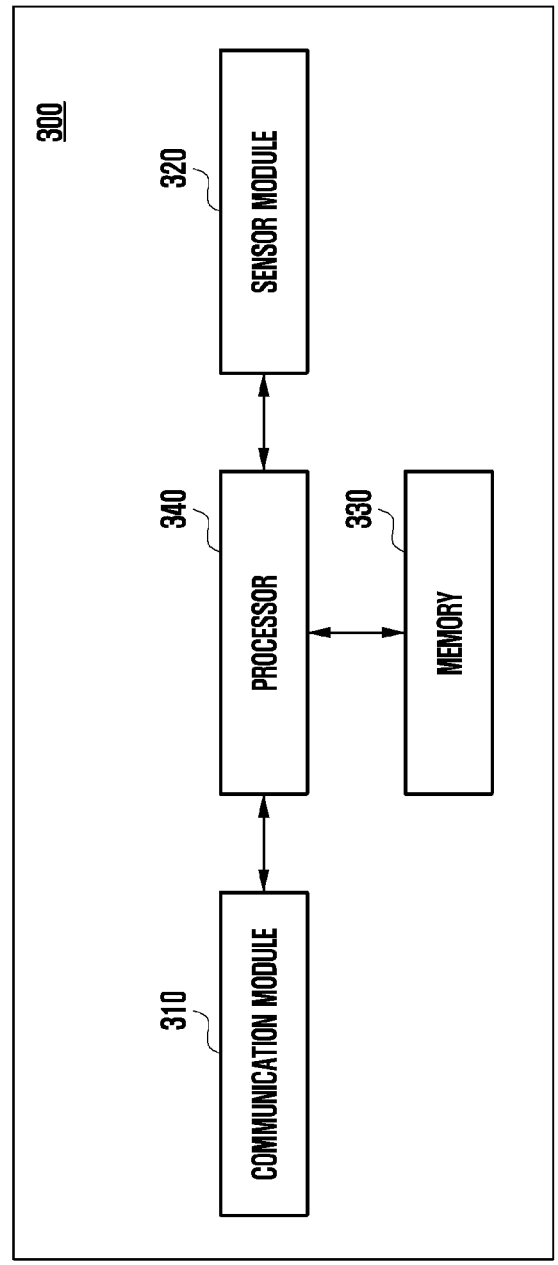
FIG. 3 is a block diagram of an electronic device according to an embodiment of the disclosure.

FIG. 3 is a block diagram of an electronic device according to an embodiment of the disclosure.

Referring to FIG. 3, an electronic device 300 (e.g., the electronic device 101 of FIG. 1 or the electronic device 210 of FIG. 2) may include a communication module 310, a sensor module 320, a memory 330, and a processor 340, and even if at least some of the illustrated components are omitted or substituted, it will not interfere with implementing various embodiments of the disclosure. The electronic device 300 according to various embodiments may include all or part of the configuration and/or functions of the electronic device 101 of FIG. 1. The electronic device 300 according to various embodiments may include all or part of the configuration and/or functions of the electronic device 210 of FIG. 2.

According to various embodiments, the communication module 310 may perform communication connection with various electronic devices (e.g., the first external electronic device 220 and/or the second external electronic device 230 of FIG. 2). The communication module 310 may include at least a part of functions and/or configurations of the communication module 190 of FIG. 1.

According to various embodiments, the communication module 310 may support short-range wireless communication (e.g., the first network 198 of FIG. 1) and may perform connection with an external electronic device (e.g., the first external electronic device 220 and/or the second external electronic device 230 of FIG. 2) using short-range wireless communication. According to various embodiments, the electronic device 300 may be connected to an external electronic device (e.g., the first external electronic device 220 and/or the second external electronic device 230) using short-range wireless communication such as Bluetooth™, Bluetooth low energy (BLE), or wireless-fidelity (Wi-Fi). According to various embodiments, the electronic device 300 may be connected to an external electronic device using short-range wireless communication to control the operation of the external electronic device (e.g., the first external electronic device 220 and/or the second external electronic device 230 of FIG. 2), and may receive data (e.g., first sensor data 221 and/or second sensor data 231) from the external electronic device (e.g., the first external electronic device 220 and/or the second external electronic device 230 of FIG. 2) or transmit various types of information including data (e.g., synchronization signal) for controlling the external electronic device to the external electronic device (e.g., the first external electronic device 220 and/or the second external electronic device 230 of FIG. 2).

According to various embodiments, the sensor module 320 may detect an operating state (e.g., power or temperature) of the electronic device 300 or an external environmental state (e.g., user state), and may generate an electrical signal or data value corresponding to the sensed state. The sensor module 320 may include at least a part of the function and/or configuration of the sensor module 176 of FIG. 1. According to an embodiment, the sensor module 320 may include, for example, a heart rate sensor, an electrocardiogram (ECG) sensor, a photoplethysmography (PPG) sensor, a gesture sensor, a gyro sensor, a barometric pressure sensor, a magnetic sensor, an acceleration sensor, a grip sensor, a proximity sensor, a color sensor, an infrared (IR) sensor, a biometric sensor, a temperature sensor, a humidity sensor, or an illuminance sensor. According to various embodiments, the sensor module 320 may generate sensing information for determining a user's state, a user's location, and/or a user's motion (e.g., gestures) by using various provided sensors. According to various embodiments, the sensor module 320 may generate sensor data (e.g., third sensor data 211). According to various embodiments, the sensor module 320 may continuously generate an analog electrical signal by driving a sensor included in the sensor module 320, and the sensor module 320 may digitize the generated analog electrical signal by sampling according to a predetermined sampling period. According to an embodiment, an analog-to-digital converter (ADC), not illustrated, included in the sensor module 320 may sample the analog signal measured by the sensor included in the sensor module 320 according to a predetermined period (e.g., the third sampling cycle) and convert the sampled analog signal into a digital signal. Alternatively, the processor 340 may convert the analog signal generated by the sensor module 320 into a digital signal. The third sensor data may be a digital signal converted from an analog signal by the sensor module 320 or the processor 340.

According to various embodiments, the memory 330 is for temporarily or permanently storing digital data, and may include at least some of the configuration and/or functions of the memory 130 of FIG. 1. In addition, the memory 330 may store at least a part of the program 140 of FIG. 1. The memory 330 may store various instructions that may be executed by the processor 340. Such instructions may include control commands such as logical operations and data input/output that may be recognized and executed by the processor 340. There is no limitation on the type and/or amount of data that the memory 330 can store, but in the disclosure, only a method for synchronizing time of different data received or obtained by the electronic device 300 according to various embodiments and a configuration and function of the memory 330 related to an operation of the processor 340 performing the method will be described. According to various embodiments, the memory 330 may previously store sampling information (e.g., sampling period information, sampling frequency information and/or count information) of each of a plurality of sensor data (e.g., the first sensor data 221, the second sensor data 231 and/or the third sensor data 211 of FIG. 2) received or obtained by the electronic device 300, for example, sampling period information (e.g., first sampling period information, second sampling period information, and/or third sampling period information). According to various embodiments, the memory 330 may store sensor data (e.g., the first sensor data 221, the second sensor data 231 and/or the third sensor data 211 of FIG. 2) received or obtained by the electronic device 300. According to various embodiments, the memory 330 may update and store sampling period information corrected from pre-stored sampling period information.

According to various embodiments, the processor 340 may process operations or data related to control and/or communication of respective components of the electronic device 300. The processor 340 may include at least some of the configuration and/or functions of the processor 120 of FIG. 1. The processor 340 may be operatively, electrically and/or functionally connected to components of the electronic device 300 such as the communication module 310, the sensor module 320, and the memory 330. There is no limitation on the type and/or amount of operations, calculations, and data processing that the processor 340 can perform, but in the disclosure, only a method for synchronizing time of different data received or obtained by the electronic device 300 according to various embodiments and a configuration and function of the processor 340 performing the method will be described.

According to various embodiments, the processor 340 may periodically transmit a synchronization signal to a plurality of external electronic devices (e.g., the first external electronic device 220 and/or the second external electronic device 230 of FIG. 2).

The synchronization signal may be a signal that causes the electronic device 300 and the external electronic device (e.g., the first external electronic device 220 and/or the second external electronic device 230 of FIG. 2) to generate constant data. For example, the synchronization signal may be a signal that causes the processor 340 to generate and include certain data (e.g., synchronization markers) in the sensor data in order to synchronize the sensor data (e.g., the first sensor data 221 and the second sensor data 231 of FIG. 2) received from each external electronic device (e.g., the first external electronic device 220 and the second external electronic device 230 of FIG. 2) and/or the sensor data (e.g., the third sensor data 211 of FIG. 2) directly generated by the electronic device 300 with each other. According to an embodiment, the synchronization signal may be a signal that causes the received external electronic device (e.g., first external electronic device 220 and/or second external electronic device 230) to generate a synchronization marker in the first sensor data 221 and/or second sensor data 231. According to an embodiment, the synchronization signal may be a signal that causes the received external electronic device (e.g., first external electronic device 220 and/or second external electronic device 230) to configure a synchronization mark on data sampled immediately before or after receiving the synchronization signal. According to an embodiment, the processor 340 may insert identification (ID) data into the synchronization signal corresponding to the timing of generating the synchronization signal. The ID of the synchronization signal may refer to, for example, an order of generation and transmission of the synchronization signal, or may correspond to a generation and transmission time of the synchronization signal. According to an embodiment, the processor 340 may periodically transmit a synchronization signal. According to an embodiment, the processor 340 may periodically and continuously generate a synchronization signal and transmit the synchronization signal to each of the external electronic devices (e.g., first external electronic device 220 and/or second external electronic device 230).

The synchronization marker may be data capable of confirming the arrival time of the synchronization signal.

For example, the synchronization marker may be unique data for identifying sample data sampled at a specific point in time. The sensor data (e.g., the first sensor data 221, the second sensor data 231 and/or the third sensor data 211 of FIG. 2) may be a set of a plurality of sample data continuously sampled according to each specific sampling period, and the synchronization marker may correspond to an identifier for identifying sample data sampled at a specific time point. According to an embodiment, the synchronization marker may include an identification (ID) corresponding to the transmission or reception time of the synchronization signal. According to an embodiment, the processor 340 may generate and transmit a signal that causes the external electronic device (e.g., first external electronic device 220 and/or second external electronic device 230) to generate a marker ID corresponding to the ID of the synchronization signal by including the ID in the synchronization marker. According to an embodiment, the external electronic device (e.g., first external electronic device 220 and/or second external electronic device 230) may generate the synchronization marker by a method of defining which value of the sensor data corresponds to the synchronization marker. In this case, a value of a predetermined interval included in the sensor data may be an index. According to an embodiment, the index may be a natural number or may correspond to an absolute or relative time stamp. The absolute time stamp may be, for example, a period calculated by each electronic device based on a standard time such as coordinated universal time (UTC). Alternatively, the time of the base station may be used as a relative time stamp. The relative time stamp may refer to a time after a specific point in time. According to an embodiment, the external electronic device (e.g., first external electronic device 220 and/or second external electronic device 230) may generate a synchronization marker by updating an identifiable specific value. For example, the external electronic device may determine that the value is arbitrarily modified according to a predetermined condition in the electronic device 210, and may generate a synchronization marker capable of restoring and identifying the original value by assigning a specific sign (e.g., a negative sign like '−') to the data value corresponding to the part where the marker exists, or by adding or encrypting an arbitrary number.

According to various embodiments, when the processor 340 generates and transmits the synchronization signal, the processor 340 may be receiving first sensor data 221 and/or second sensor data 231 from the external electronic device (e.g., first external electronic device 220 and/or second external electronic device 230) through the communication module 310. According to various embodiments, the processor 340 may be generating sensor data (e.g., third sensor data) through the sensor module 320 at the time of generating and transmitting the synchronization signal. According to an embodiment, the processor 340 may be continuously obtaining sensor data while generating and transmitting a synchronization signal.

According to various embodiments, the processor 340 may transmit a synchronization signal to the external electronic device (e.g., first external electronic device 220 and/or second external electronic device 230) and configure a synchronization marker in the sensor data (e.g., third sensor data) being generated. According to an embodiment, the processor 340 may generate the synchronization marker immediately before the transmission time, immediately after the transmission time, or simultaneously with the transmission time, in response to the transmission time of the synchronization signal. The processor 340 may generate a synchronization marker by including a marker ID corresponding to the ID of the generated and transmitted synchronization signal in the synchronization marker.

According to various embodiments, the processor 340 may obtain and store sensor data including a synchronization marker. According to various embodiments, the processor 340 may receive sensor data (e.g., the first sensor data 221 and/or the second sensor data 231 of FIG. 2) including a synchronization marker from an external electronic device (e.g., the first external electronic device 220 and/or the second external electronic device 230 of FIG. 2). The synchronization marker may be, for example, data generated by each external electronic device (e.g., first external electronic device 220 and second external electronic device 230) in response to a synchronization signal transmitted by the processor 340 and included in the first sensor data 221 and second sensor data 231. According to various embodiments, the processor 340 may generate a synchronization marker in response to generation or transmission of a synchronization signal, and include the generated synchronization marker in the generated sensor data (e.g., the first sensor data 221 of FIG. 2). According to various embodiments, the processor 340 may store the obtained sensor data (e.g., first sensor data 221, second sensor data 231 and/or third sensor data 211) including the synchronization marker in the memory 330.

According to various embodiments, the processor 340 may select reference data. The reference data may be data to be a reference for synchronization among a plurality of sensor data obtained and stored by the processor 340.

For example, the reference data may refer to data serving as a synchronization reference among obtained sensor data, that is, first sensor data 221 and/or second sensor data 231 received from an external electronic device (e.g., first external electronic device 220 and/or second external electronic device 230), and/or sensor data (e.g., third sensor data) generated by the electronic device 300. According to various embodiments, the processor 340 may check a sampling period of each connected external electronic device (e.g., the first external electronic device 220 and the second external electronic device 230 of FIG. 2) and select reference data based on an error rate of the sampling period (e.g., first sampling period and second sampling period). According to an embodiment, the processor 340 may check error rate information about the sampling period of each external electronic device (e.g., first external electronic device 220 and second external electronic device 230) stored in the memory 330, and select reference data based on the checked error rate information. According to an embodiment, the processor 340 may select sensor data of an external electronic device having a lower sampling period error rate as reference data. According to various embodiments, the processor 340 may select sensor data (e.g., the third sensor data 211) generated by the electronic device 300 as reference data. According to an embodiment, when the sensor data (e.g., third sensor data) measured by the electronic device 300 is synchronized together with the sensor data (e.g., first sensor data and/or second sensor data) of the external electronic device (e.g., first external electronic device 220 and/or second external electronic device 230), the sensor data (e.g., third sensor data) measured by the electronic device 300 may be preferentially selected as reference data. According to an embodiment, the processor 340 may compare the sampling period error rate of the external electronic device (e.g., first external electronic device 220 and/or second external electronic device 230) and the sampling period error rate of the electronic device 300 and select reference data based on the compared error rate.

According to various embodiments, the processor 340 may detect a synchronization marker. The processor 340 may detect a synchronization marker included in the obtained sensor data (e.g. first sensor data, second sensor data and/or third sensor data). The detection of the synchronization marker may be an operation of checking a position of sample data including the synchronization marker. According to an embodiment, the processor 340 may detect the synchronization marker by checking the position of the synchronization marker included in each sensor data (e.g. first sensor data, second sensor data and/or third sensor data). According to various embodiments, each of the plurality of sensor data (e.g., first sensor data, second sensor data and/or third sensor data) may include a plurality of synchronization markers, and the processor 340 may detect the plurality of synchronization markers. According to an embodiment, the processor 340 may detect only the synchronization marker of the section to be synchronized based on the marker ID included in the synchronization marker.

According to various embodiments, the processor 340 may align a plurality of sensor data (e.g., first sensor data, second sensor data and/or third sensor data). According to various embodiments, the synchronization markers included in each sensor data (e.g., first sensor data, second sensor data and/or third sensor data) may include the same marker ID in response to the same synchronization signal, and the processor 340 may align each sensor data (e.g., first sensor data, second sensor data and/or third sensor data) based on a synchronization marker having the same marker ID using the marker ID. According to an embodiment, the electronic device 300 may receive even the same synchronization marker at different times for each sensor data. For example, the same synchronization marker may be received at different times due to factors such as a communication state, a processing speed of the processor 340, and a processing speed of an external electronic device. According to an embodiment, the processor 340 may align the plurality of sensor data (e.g., first sensor data, second sensor data and/or third sensor data) based on the positions of the synchronization markers having the same marker ID. According to an embodiment, the processor 340 may align the plurality of sensor data (e.g., first sensor data, second sensor data and/or third sensor data) based on the positions of the synchronization markers included in the reference data.

According to various embodiments, the processor 340 may calculate a required time between synchronization markers of the reference data. According to various embodiments, each of the plurality of sensor data (e.g., first sensor data, second sensor data and/or third sensor data) may include a plurality of synchronization markers, and an interval between the synchronization markers may be calculated as time. According to various embodiments, the processor 340 may calculate a required time between the synchronization markers with respect to at least two synchronization markers included in the reference data. According to various embodiments, the processor 340 may determine the number of pieces of sample data of the reference data included between the synchronization markers detected in the reference data, and may calculate an interval between the synchronization markers of the reference data based on the determined number of pieces of sample data and the sampling period information of the reference data stored in advance in the memory 330. According to an embodiment, the processor 340 may calculate a required time between the synchronization markers by multiplying the number of sampling data included between the synchronization markers by the sampling period information of the reference data based on the positions of the synchronization markers included in the reference data. According to an embodiment, when the sensor data (e.g., third sensor data) directly generated by the electronic device 300 is selected as the reference data, the processor 340 may obtain a required time based on a time point of generation or transmission of a synchronization signal corresponding to each synchronization marker.

According to various embodiments, the processor 340 may correct the sampling period information and store the corrected sampling period information. According to various embodiments, the processor 340 may correct sampling period information of sensor data other than the reference data based on the sampling period information of the reference data. According to various embodiments, the processor 340 may correct the sampling period information of the sensor data other than the reference data based on the calculated required time and the synchronization marker positions of the sensor data other than the reference data. According to an embodiment, even in the case of different sensor data, the time at which the synchronization marker is generated may be considered to be substantially the same. Therefore, the physically required time between synchronization markers may be considered as substantially the same as even between different sensor data. However, due to the error rate of the sensor, the sensor of each external electronic device (e.g., the first external electronic device 220 and/or the second external electronic device 230 of FIG. 2) may perform sampling at a sampling cycle different from the sampling cycle information (e.g., first sampling period information and/or second sampling period information) stored in the memory 330. Accordingly, it is possible to set the sampling period information of the reference data stored in the memory 330 as a true value, and correct the sampling period information of the sensor data other than the reference data. According to various embodiments, the processor 340 may correct sampling period information of the sensor data other than the reference data based on the calculated required time and the number of pieces of sample data between the synchronization markers of the sensor data other than the reference data. According to an embodiment, the processor 340 may determine that the required time calculated using the reference data is the same as the required time between synchronization markers of sensor data other than the reference data. Accordingly, when the number of pieces of sample data between synchronization markers is divided with respect to the calculated required time, corrected sampling period information may be obtained. According to an embodiment, the processor 340 may check the number of pieces of sample data between the detected synchronization markers with respect to the remaining sensor data other than the reference data, and obtain corrected sampling period information based on the checked number of pieces of sample data. According to an embodiment, the processor 340 may store the corrected sampling period information in the memory 330. According to an embodiment, the processor 340 may update the pre-stored sampling period information with the corrected sampling period information and store the corrected sampling period information in the memory 330. According to an embodiment, the processor 340 may analyze each sensor data using the corrected sampling period information, and may perform synchronization between the plurality of sensor data.

Figure 4:
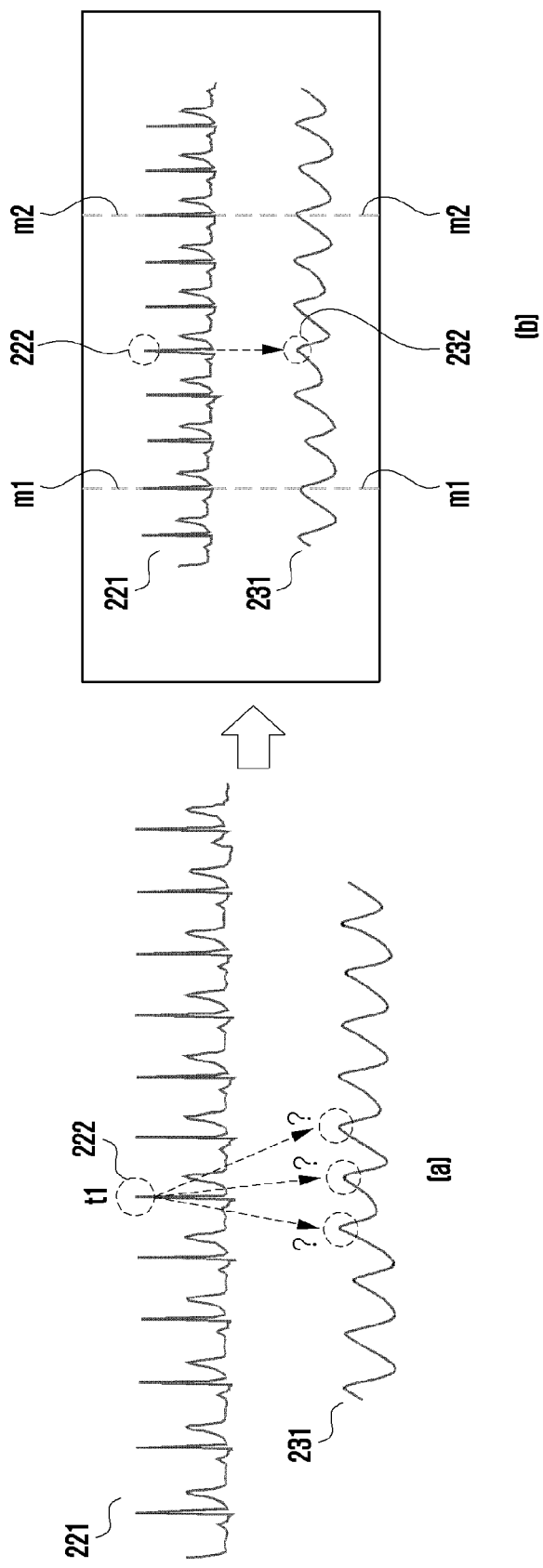
FIG. 4 is an example of synchronizing different sensor data according to an embodiment of the disclosure.

FIG. 4 is an example of synchronizing different sensor data according to an embodiment of the disclosure.

Referring to the identification code in part (a) of FIG. 4, this may be a case of comparing two sensor data (e.g., first sensor data 221 and second sensor data 231) before synchronization. Referring to part (a) of FIG. 4, the first sensor data 221 and the second sensor data 231 may be data measured using different sensors. For example, the first sensor data 221 may be sensor data measured using a first external electronic device (e.g., the first external electronic device 220 of FIG. 2), and the second sensor data 231 may be sensor data measured using a second external electronic device (e.g., the second external electronic device 230 of FIG. 2), or the first sensor data and the second sensor data may be sensor data received by the electronic devices (e.g., the electronic device 210 of FIG. 2 and/or the electronic device 300 of FIG. 3) from each of the external electronic devices (e.g., first external electronic device 220 and second external electronic device 230). According to an embodiment, the first sensor data 221 and the second sensor data 231 may be data obtained by measuring different bio-signals of the same user using different sensors. For example, the first sensor data 221 may be data obtained by measuring an electrocardiogram (ECG), and the second sensor data 231 may be data obtained by measuring a photoplethysmography (PPG). Referring to part (a) of FIG. 4, a specific event occurs to the user at time t1, and there may be a need to analyze the first sensor data 221 and the second sensor data 231 at time t1. In the case of the sensor data before correction, if synchronization is not achieved due to an error in the sampling period of the sensors of each device (e.g., the first external electronic device 220 and the second external electronic device 230), comparative analysis may be difficult. Referring to part (a) of FIG. 4, when the reference data is selected as the first sensor data 221, it may be difficult to determine the area of the second sensor data 231 corresponding to an area 222 of the first sensor data at time t1.

Referring to the identification code in part (b) of FIG. 4, this may be an example of correcting sampling period information of the second sensor data 231 by selecting the first sensor data 221 as reference data. The first sensor data 221 and the second sensor data 231 may be synchronized with each other based on the positions of the respective synchronization markers (e.g., first synchronization marker m1 and second synchronization marker m2) included in the first sensor data 221 and the second sensor data 231. According to an embodiment, based on the number of pieces of sample data between the first synchronization marker m1 and second synchronization marker m2 of the reference data (e.g., first sensor data 221) and the sampling period information (e.g., first sampling period information T1) of the first sensor data 221 stored in the memory (e.g., memory 330 in FIG. 3), the required time between the synchronization markers (e.g., first synchronization marker m1 and second synchronization marker m2) of the first sensor data 221 may be calculated. According to an embodiment, the corrected sampling period information (e.g., corrected second sampling period information T2') of the second sensor data 231 may be calculated based on the calculated time between the markers (e.g., first synchronization marker m1 and second synchronization marker m2) based on the first sensor data 221 and the number of pieces of sample data between the markers (e.g., first synchronization marker m1 and second synchronization marker m2) of the second sensor data 231. According to an embodiment, the processor (e.g., the processor 340 of FIG. 3) of the electronic device 300 may update the sampling period information (e.g., second sampling period information T2) of the second sensor data 231 previously stored in the memory 330 to the corrected sampling period information (e.g., corrected second sampling period information T2') and store the updated information in the memory 330. According to an embodiment, by applying the corrected sampling period information (e.g., corrected second sampling period information T2') to the second sensor data 231, an area 232 of the second sensor data corresponding to the area 222 of the first sensor data at time t1 may be checked, and the first sensor data 221 and the second sensor data 231 may be compared and analyzed.

Figure 5:
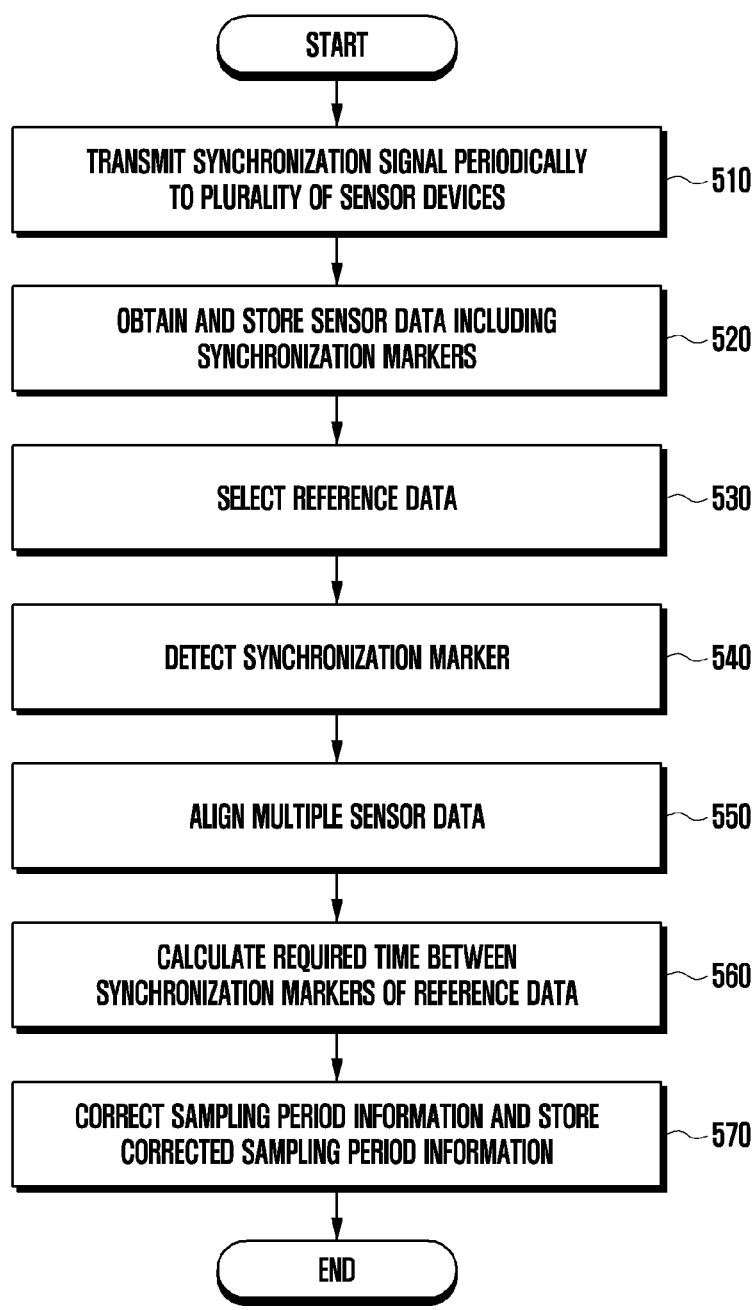
FIG. 5 is a flowchart illustrating an operation in which an electronic device synchronizes different sensor data according to an embodiment of the disclosure.

FIG. 5 is a flowchart illustrating an operation in which an electronic device (e.g., an electronic device of FIG. 3) synchronizes different sensor data according to an embodiment of the disclosure.

Referring to FIG. 5, the operation of synchronizing different sensor data of FIG. 5 may be described as each operation performed by the processor of an electronic device 300 (e.g., a processor 340 of FIG. 3).

Referring to operation 510, the processor 340 may periodically transmit a synchronization signal to a plurality of external electronic devices (e.g., the first external electronic device 220 and the second external electronic device 230 of FIG. 2).

The synchronization signal may be a signal that causes the electronic device 300 and the external electronic device (e.g., the first external electronic device 220 and/or the second external electronic device 230 of FIG. 2) to generate constant data. For example, the synchronization signal may be a signal that causes the processor 340 to generate and include certain data (e.g., synchronization markers) in the sensor data in order to synchronize the sensor data (e.g., the first sensor data 221 and/or the second sensor data 231 of FIG. 2) received from each external electronic device (the first external electronic device 220 and/or the second external electronic device 230 of FIG. 2) and/or the sensor data (e.g., the third sensor data 211 of FIG. 2) directly generated by the electronic device 300 with each other. According to an embodiment, the synchronization signal may be a signal that causes the received external electronic device (e.g., first external electronic device 220 and/or second external electronic device 230) to generate a synchronization marker in the first sensor data 221 and/or second sensor data 231. According to an embodiment, the synchronization signal may be a signal that causes the received external electronic device (e.g., first external electronic device 220 and/or second external electronic device 230) to configure a synchronization marker on data sampled immediately before or after receiving the synchronization signal. According to an embodiment, the external electronic device (e.g., first external electronic device 220 and/or second external electronic device 230) may be a device that generates sensor data at high speed. For example, the external electronic device (e.g., first external electronic device 220 and/or second external electronic device 230 may be generating sensor data using a frequency of tens to hundreds of hertz (Hz) or higher. Accordingly, the difference between the time points immediately before or immediately after reception of the synchronization signal may be very small, or the time points immediately before or immediately after reception of the synchronization signal may be substantially the same. According to an embodiment, the processor 340 may insert identification (ID) data into the synchronization signal corresponding to the timing of generating the synchronization signal. The ID of the synchronization signal may refer to, for example, an order of generation and transmission of the synchronization signal, or may correspond to a generation and transmission time of the synchronization signal. According to an embodiment, the processor 340 may periodically transmit a synchronization signal. According to an embodiment, the processor 340 may periodically and continuously generate a synchronization signal and transmit the synchronization signal to each of the external electronic devices (e.g., first external electronic device 220 and/or second external electronic device 230).

The synchronization marker may be data capable of confirming the arrival time of the synchronization signal.

For example, the synchronization marker may be unique data for identifying sample data, sampled at a specific point in time. The sensor data (e.g., the first sensor data 221, the second sensor data 231 and/or the third sensor data 211 of FIG. 2) may be a set of a plurality of sample data continuously sampled according to each specific sampling period, and the synchronization marker may correspond to an identifier for identifying sample data sampled at a specific time point. According to an embodiment, the synchronization marker may include an identification (ID) corresponding to the transmission or reception time of the synchronization signal. According to an embodiment, the processor 340 may generate and transmit a signal that causes the external electronic device (e.g., first external electronic device 220 and/or second external electronic device 230) to generate a marker ID corresponding to the ID of the synchronization signal by including the marker ID in the synchronization marker.

According to various embodiments, when the processor 340 generates and transmits the synchronization signal, the processor 340 may be receiving first sensor data 221 and/or second sensor data 231 from the external electronic device (e.g., first external electronic device 220 and/or second external electronic device 230) through the communication module (e.g., the communication module 310 of FIG. 3). According to various embodiments, the processor 340 may be generating sensor data (e.g., third sensor data) through the sensor module (e.g., the sensor module 320 of FIG. 3) at the time of generating and transmitting the synchronization signal. According to an embodiment, the processor 340 may be continuously obtaining sensor data while generating and transmitting a synchronization signal.

According to various embodiments, the processor 340 may transmit a synchronization signal to the external electronic device (e.g., first external electronic device 220 and/or second external electronic device 230) and configure a synchronization marker in the sensor data (e.g., third sensor data) being generated. According to an embodiment, the processor 340 may generate the synchronization marker immediately before the transmission time, immediately after the transmission time, or simultaneously with the transmission time, in response to the transmission time of the synchronization signal. The processor 340 may generate a synchronization marker by including a marker ID corresponding to the ID of the generated and transmitted synchronization signal in the synchronization marker.

Referring to operation 520, the processor 340 may obtain and store sensor data including a synchronization marker. According to various embodiments, the processor 340 may receive sensor data (e.g., the first sensor data 221 and/or the second sensor data 231 of FIG. 2) including a synchronization marker from an external electronic device (e.g., the first external electronic device 220 and/or the second external electronic device 230 of FIG. 2). The synchronization marker may be, for example, data generated by each external electronic device (e.g., first external electronic device 220 and/or second external electronic device 230) in response to a synchronization signal transmitted by the processor 340 and included in the first sensor data 221 and/or second sensor data 231. According to various embodiments, the processor 340 may generate a synchronization marker in response to generation or transmission of a synchronization signal, and include the generated synchronization marker in the generated sensor data (e.g., the first sensor data 221 of FIG. 2). According to various embodiments, the processor 340 may store the obtained sensor data (e.g., first sensor data 221, second sensor data 231 and/or third sensor data 211) including the synchronization marker in the memory 330.

Referring to operation 530, the processor 340 may select reference data. The reference data may be data to be a reference for synchronization among a plurality of sensor data obtained and stored by the processor 340.

For example, the reference data may refer to data serving as a synchronization reference among obtained sensor data, that is, first sensor data 221 and/or second sensor data 231 received from an external electronic device (e.g., first external electronic device 220 and/or second external electronic device 230) and/or sensor data (e.g., third sensor data) generated by the electronic device 300. According to various embodiments, the processor 340 may check a sampling period of each connected external electronic device (e.g., the first external electronic device 220 and the second external electronic device 230 of FIG. 2) and select reference data based on an error rate of the sampling period (e.g., first sampling period and second sampling period). According to an embodiment, the processor 340 may check error rate information about the sampling period of each external electronic device (e.g., first external electronic device 220 and second external electronic device 230) stored in the memory 330, and select reference data based on the checked error rate information. According to an embodiment, the processor 340 may select sensor data of an external electronic device having a lower sampling period error rate as reference data. According to various embodiments, the processor 340 may select sensor data (e.g., the third sensor data 211) generated by the electronic device 300 as reference data. According to an embodiment, when the sensor data (e.g., third sensor data) measured by the electronic device 300 is synchronized together with the sensor data (e.g., first sensor data and/or second sensor data) of the external electronic device (e.g., first external electronic device 220 and/or second external electronic device 230), the sensor data (e.g., third sensor data) measured by the electronic device 300 may be preferentially selected as reference data. According to an embodiment, the processor 340 may compare the sampling period error rate of the external electronic device (e.g., first external electronic device 220 and/or second external electronic device 230) and the sampling period error rate of the electronic device 300 and select reference data based on the compared error rate.

Referring to operation 540, the processor 340 may detect a synchronization marker. The processor 340 may detect a synchronization marker included in the obtained sensor data (e.g. first sensor data, second sensor data and/or third sensor data). The detection of the synchronization marker may be an operation of checking a position of sample data including the synchronization marker. According to an embodiment, the processor 340 may detect the synchronization marker by checking the position of the synchronization marker included in each sensor data (e.g. first sensor data, second sensor data and/or third sensor data). According to various embodiments, each of the plurality of sensor data (e.g., first sensor data, second sensor data and/or third sensor data) may include a plurality of synchronization markers, and the processor 340 may detect the plurality of synchronization markers. According to an embodiment, the processor 340 may detect only the synchronization marker of the section to be synchronized based on the marker ID included in the synchronization marker.

Referring to operation 550, the processor 340 may align a plurality of sensor data (e.g., first sensor data, second sensor data and/or third sensor data). According to various embodiments, the synchronization markers included in each sensor data (e.g., first sensor data, second sensor data and/or third sensor data) may include the same marker ID in response to the same synchronization signal, and the processor 340 may align each sensor data (e.g., first sensor data, second sensor data and/or third sensor data) based on a synchronization marker having the same marker ID using the marker ID. According to an embodiment, the electronic device 300 may receive even the same synchronization marker at different times for each sensor data. For example, the same synchronization marker may be received at different times due to factors such as a communication state, a processing speed of the processor 340, and a processing speed of an external electronic device. According to an embodiment, the processor 340 may align the plurality of sensor data (e.g., first sensor data, second sensor data and/or third sensor data) based on the positions of the synchronization markers having the same marker ID. According to an embodiment, the processor 340 may align the plurality of sensor data (e.g., first sensor data, second sensor data and/or third sensor data) based on the positions of the synchronization markers included in the reference data.

Referring to operation 560, according to various embodiments, the processor 340 may calculate a required time between synchronization markers of the reference data. According to various embodiments, each of the plurality of sensor data (e.g., first sensor data, second sensor data and/or third sensor data) may include a plurality of synchronization markers, and an interval between the synchronization markers may be calculated as time. According to various embodiments, the processor 340 may calculate a required time between the synchronization markers with respect to at least two synchronization markers included in the reference data. According to various embodiments, the processor 340 may determine the number of pieces of sample data of the reference data included between the synchronization markers detected in the reference data, and may calculate an interval between the synchronization markers of the reference data based on the determined number of pieces of sample data and the sampling period information of the reference data stored in advance in the memory 330. According to an embodiment, the processor 340 may calculate a required time between the synchronization markers by multiplying the number of sampling data included between the synchronization markers by the sampling period information of the reference data based on the positions of the synchronization markers included in the reference data. According to an embodiment, when the sensor data (e.g., third sensor data) directly generated by the electronic device 300 is selected as the reference data, the processor 340 may obtain a required time based on a time point of generation or transmission of a synchronization signal corresponding to each synchronization marker.

Referring to operation 570, the processor 340 may correct the sampling period information and store the corrected sampling period information. According to various embodiments, the processor 340 may correct sampling period information of sensor data other than the reference data based on the sampling period information of the reference data. According to various embodiments, the processor 340 may correct the sampling period information of the sensor data other than the reference data based on the calculated required time and the synchronization marker positions of the sensor data other than the reference data. According to an embodiment, even in the case of different sensor data, the time at which the synchronization marker is generated may be considered to be substantially the same. Therefore, it may be considered that the physical required time between synchronization markers is substantially the same even between different sensor data. However, due to the error rate of the sensor, the sensor of each external electronic device (e.g., the first external electronic device 220 and/or the second external electronic device 230 of FIG. 2) may perform sampling at a sampling cycle different from the sampling cycle information (e.g., first sampling period information and/or second sampling period information) stored in the memory 330. Accordingly, it is possible to set the sampling period information of the reference data stored in the memory 330 as a true value, and correct the sampling period information of the sensor data other than the reference data. According to various embodiments, the processor 340 may correct sampling period information of the sensor data other than the reference data based on the calculated required time and the number of pieces of sample data between the synchronization markers of the sensor data other than the reference data. According to an embodiment, the processor 340 may determine that the required time calculated using the reference data is the same as the required time between synchronization markers of sensor data other than the reference data. Accordingly, when the number of pieces of sample data between synchronization markers is divided with respect to the calculated required time, corrected sampling period information may be obtained. According to an embodiment, the processor 340 may check the number of pieces of sample data between the detected synchronization markers with respect to the remaining sensor data other than the reference data, and obtain corrected sampling period information based on the checked number of pieces of sample data. According to an embodiment, the processor 340 may store the corrected sampling period information in the memory 330. According to an embodiment, the processor 340 may update the pre-stored sampling period information with the corrected sampling period information and store the corrected sampling period information in the memory 330. According to an embodiment, the processor 340 may analyze each sensor data using the corrected sampling period information, and may perform synchronization between the plurality of sensor data.

Figure 6A:
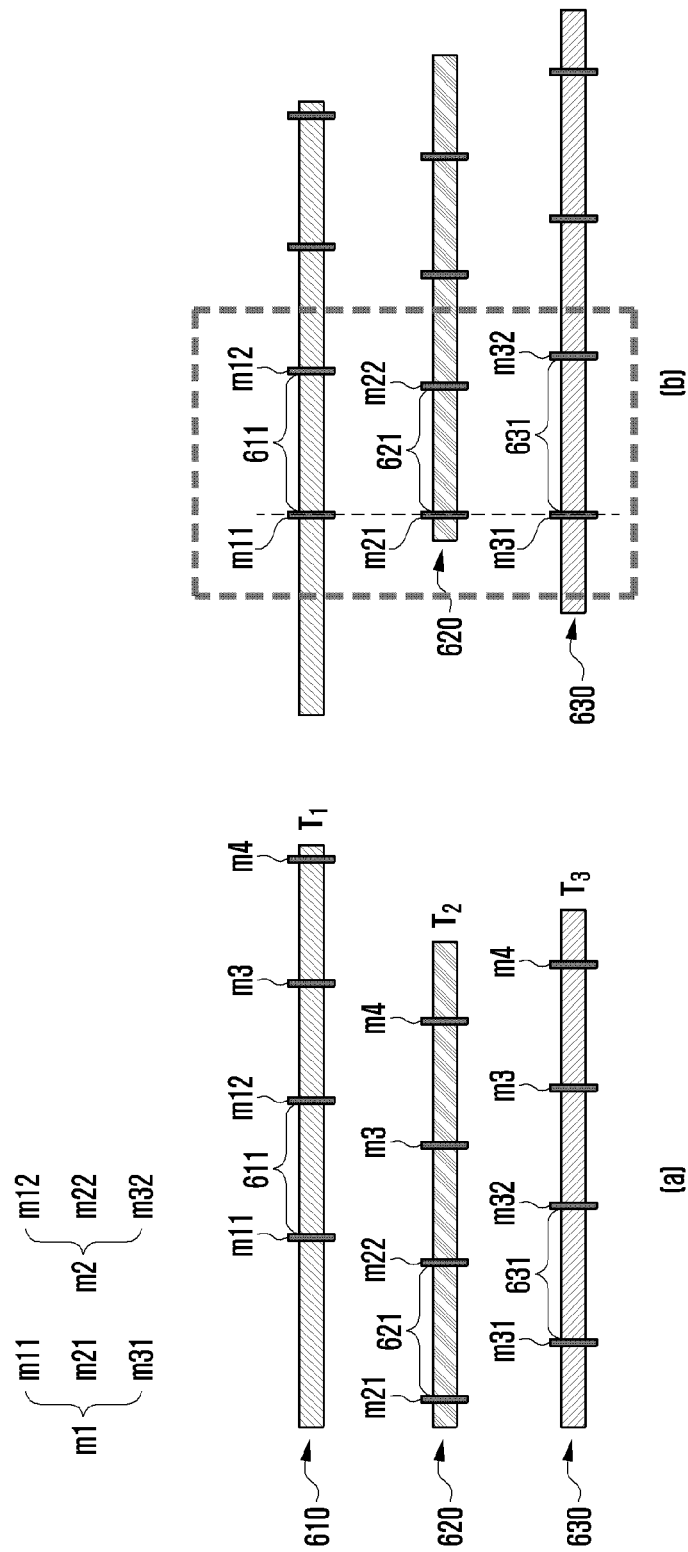
FIGS. 6A and 6B are examples of methods for synchronizing different sensor data according to various embodiments of the disclosure.
Figure 6B:
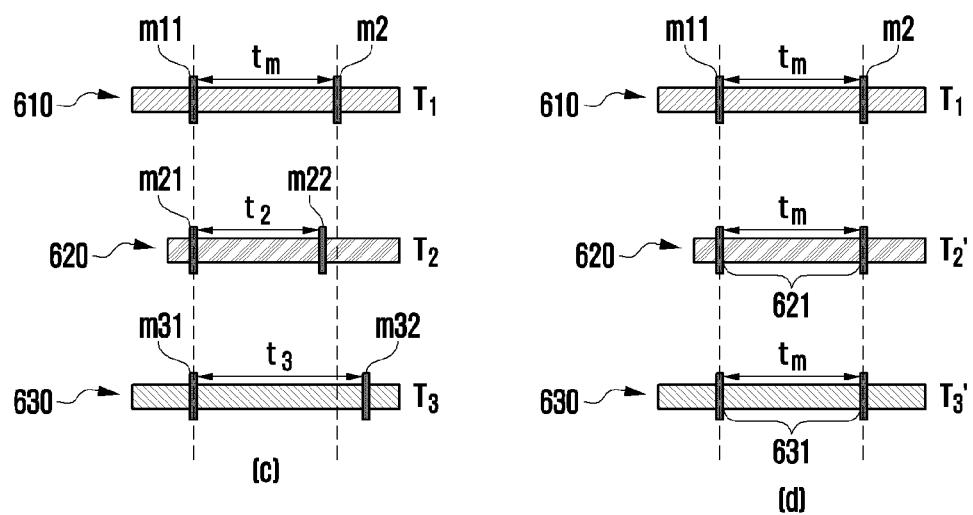

FIGS. 6A and 6B are examples of methods for synchronizing different sensor data according to various embodiments of the disclosure.

Referring to FIGS. 6A and 6B, identification codes may be diagrams representing sensor data (e.g., first sensor data 610, second sensor data 620, and third sensor data 630) measured and sampled from different devices, respectively.

For example, a first identification code may correspond to first sensor data 610, a second identification code may correspond to second sensor data 620, and a third identification code may correspond to third sensor data 630. The first sensor data 610, the second sensor data 620, and the third sensor data 630 may correspond to sensor data received or generated and obtained by the electronic device (e.g., the electronic device 300 of FIG. 3).

Referring to part (a) of FIG. 6A, in order for the electronic device 300 to perform analysis using the plurality of sensor data (e.g., first sensor data 610, second sensor data 620, and third sensor data 630), synchronization between the plurality of sensor data (e.g., first sensor data 610, second sensor data 620, and third sensor data 630) may be required. For example, in order to compare different sensor data for an event occurring at a specific time, there may be a need for a plurality of sensor data (e.g., first sensor data 610, second sensor data 620, and third sensor data 630) to be aligned on the same time axis. Referring to parts (a) and (b) of FIG. 6A, the electronic device 300 may synchronize the plurality of sensor data (e.g., first sensor data 610, second sensor data 620, and third sensor data 630) by calculating or correcting an error of the sampling period information (e.g., first sampling period information T1, second sampling period information T2, and third sampling period information T3) stored in the memory (e.g., memory 330 in FIG. 3) with respect to the plurality of sensor data (e.g., first sensor data 610, second sensor data 620, and third sensor data 630), and updating the error-corrected sampling period information.

Referring to part (a) of FIG. 6A, each sensor data (e.g., first sensor data 610, second sensor data 620, and third sensor data 630) may include a plurality of synchronization markers (e.g., first synchronization marker m1, second synchronization marker m2, third synchronization marker m3, and fourth synchronization marker m4). According to various embodiments, the electronic device 300 may periodically transmit a synchronization signal for generating a synchronization marker to each external electronic device (e.g., the first external electronic device 220 and the second external electronic device 230 of FIG. 2) including a sensor. According to an embodiment, the electronic device 300 may simultaneously transmit a synchronization signal to each external electronic device (e.g., the first external electronic device 220 and the second external electronic device 230 of FIG. 2). The synchronization marker may be data capable of confirming the arrival time of the synchronization signal. For example, the synchronization marker may be unique data for identifying sample data, sampled at a specific point in time. A plurality of sensor data (e.g., the first sensor data 610, the second sensor data 620 and/or the third sensor data 630) may be a set of a plurality of sample data continuously sampled according to each specific sampling period, and the synchronization marker may correspond to an identifier for identifying sample data sampled at a specific time point. According to an embodiment, the synchronization marker may include an identification (ID) corresponding to the transmission or reception time of the synchronization signal. According to an embodiment, the electronic device 300 may generate and transmit a signal that causes the external electronic device (e.g., first external electronic device 220 and/or second external electronic device 230) to generate a marker ID corresponding to the ID of the synchronization signal by including it in the synchronization marker. According to an embodiment, the electronic device 300 may generate the same synchronization marker in the sensor data being generated while transmitting the synchronization signal. Among the synchronization markers included in the plurality of sensor data (e.g., first sensor data 610, second sensor data 620, and third sensor data 630), all synchronization markers corresponding to the same synchronization signal may include the same ID. For example, a first synchronization marker m11 included in the first sensor data 610 may be the same synchronization marker as a first synchronization marker m21 included in the second sensor data 620. According to various embodiments, the plurality of sensor data (e.g., first sensor data 610, second sensor data 620, and third sensor data 630) may include a plurality of sample data between synchronization markers. For example, based on the first sensor data 610, a plurality of first sample data 611 may be included between the first synchronization marker m11 and a second synchronization marker m12. The second sensor data 620 may also include a plurality of second sample data 621 between the first synchronization marker m21 and the second synchronization marker m22, and the third sensor data 630 may also include a plurality of third sample data 631 between a first synchronization marker m31 and a second synchronization marker m32. According to various embodiments, each of the plurality of sensor data (e.g., first sensor data 610, second sensor data 620, and third sensor data 630) may be a set of data sampled with a unique sampling period. For example, the first sensor data 610 may be a set of data sampled according to the first sampling period information T1, the second sensor data 620 may be a set of data sampled according to the second sampling period information T2, and the third sensor data 630 may be a set of data sampled according to the third sampling period information T3. Sampling data (e.g., first sampling period information T1, second sampling period information T2, and third sampling period information T3) before correction may each have a unique error rate, and may be in a state requiring synchronization according to correction. According to an embodiment, sampling period information data (e.g., first sampling period information T1, second sampling period information T2, and third sampling period information T3) for each sampling period before correction may be stored in the memory (e.g., the memory 330 of FIG. 3) of the electronic device 300. According to various embodiments, the electronic device 300 may detect a synchronization marker. The electronic device 300 may detect a synchronization marker included in the obtained sensor data (e.g., the first sensor data 610, the second sensor data 620, and the third sensor data 630).

The detection of the synchronization marker may be an operation of checking a position of sample data including the synchronization marker. According to an embodiment, the electronic device 300 may detect the synchronization marker by checking the position of the synchronization marker (e.g., first synchronization marker m1, second synchronization marker m2, third synchronization marker m3, and fourth synchronization marker m4) included in each sensor data (e.g., the first sensor data 610, the second sensor data 620, and the third sensor data 630). According to various embodiments, each of the plurality of sensor data (e.g., the first sensor data 610, the second sensor data 620, and the third sensor data 630) may include a plurality of synchronization markers, and the electronic device 300 may detect the plurality of synchronization markers. According to an embodiment, the electronic device 300 may detect only the synchronization marker (e.g., first synchronization marker m1 and second synchronization marker m2) of the section to be synchronized based on the marker ID included in the synchronization marker.

Referring to part (b) of FIG. 6A, the electronic device 300 may align a plurality of sensor data (e.g., the first sensor data 610, the second sensor data 620, and the third sensor data 630). The electronic device 300 may align each sensor data (e.g., the first sensor data 610, the second sensor data 620, and the third sensor data 630) based on the synchronization marker (e.g., first synchronization marker m1) having the same marker ID by using the marker ID of the synchronization marker (e.g., first synchronization marker m1). According to an embodiment, the electronic device 300 may align the plurality of sensor data (e.g., the first sensor data 610, the second sensor data 620, and the third sensor data 630) based on the positions of the synchronization markers (e.g., first synchronization marker m1) having the same marker ID. According to an embodiment, the electronic device 300 may align the plurality of sensor data (e.g., the first sensor data 610, the second sensor data 620, and the third sensor data 630) based on the position of the synchronization marker included in the reference data. The reference data may be data to be a synchronization reference among a plurality of sensor data obtained and stored by the electronic device 300. According to various embodiments, the electronic device 300 may check a sampling period of each connected external electronic device (e.g., the first external electronic device 220 and the second external electronic device 230 of FIG. 2) and select reference data based on an error rate of the sampling period. According to an embodiment, the electronic device 300 may check error rate information about the sampling period of each external electronic device (e.g., the first external electronic device 220 and the second external electronic device 230 of FIG. 2) stored in the memory 330, and select reference data based on the checked error rate information. According to an embodiment, the electronic device 300 may select sensor data of an external electronic device having a lower sampling period error rate as reference data. According to various embodiments, the electronic device 300 may select sensor data generated by the electronic device 300 as reference data. According to an embodiment, when the sensor data measured by the electronic device 300 are synchronized together with the sensor data of the external electronic device (e.g., first external electronic device 220 and/or second external electronic device 230 of FIG. 2), the sensor data measured by the electronic device 300 may be preferentially selected as reference data. According to an embodiment, the electronic device 300 may compare the sampling period error rate of the external electronic device (e.g., first external electronic device 220 and/or second external electronic device 230 of FIG. 2) and the sampling period error rate of the electronic device 300 and select reference data based on the compared error rate. Referring to part (b) of FIG. 6A, a plurality of sensor data (e.g., the first sensor data 610, the second sensor data 620, and the third sensor data 630) may be arranged using the first sensor data 610 as reference data. According to various embodiments, the plurality of sensor data (e.g., first sensor data 610, second sensor data 620, and third sensor data 630) may be aligned based on a synchronization marker (e.g., first synchronization marker m11) included in the reference data (e.g., first sensor data 610). For example, sensor data (e.g., second sensor data 620 and third sensor data 630) other than the reference data (e.g., first sensor data 610) may be aligned based on the position of the reference data (e.g., first synchronization marker m11). Referring to part (b) of FIG. 6A, the alignment of the sensor data may refer to moving the remaining sensor data (e.g., second sensor data 620 and third sensor data 630) other than the reference data so that the same synchronization marker (e.g., the first synchronization marker of the second sensor data 620 and the first synchronization marker of the third sensor data 630) included in the remaining sensor data (e.g., second sensor data 620 and third sensor data 630) other than the reference data is disposed at the same position as the first synchronization marker m11 of the first sensor data.

Referring to part (c) of FIG. 6B, the electronic device 300 may calculate the required time tm between at least two synchronization markers (e.g., first synchronization marker m11 and second synchronization marker m12) included in the reference data (e.g., first sensor data 610). Referring to part (c) of FIG. 6B, a section requiring synchronization may be the section between the first synchronization marker m1 and the second synchronization marker m2. According to various embodiments, the electronic device 300 may calculate the required time tm between at least two synchronization markers (e.g., first synchronization marker m11 and second synchronization marker m12) in a period requiring synchronization, using markers of reference data (e.g., first sensor data 610). According to various embodiments, the electronic device 300 may check the number of pieces of sample data of the reference data (e.g., first sensor data 610) included between the synchronization markers (e.g., first synchronization marker m11 and second synchronization marker m12) detected in the reference data (e.g., first sensor data 610), and may calculate the required time tm between the synchronization markers (e.g., first synchronization marker m11 and second synchronization marker m12) of the reference data based on the checked number of pieces of sample data and the sampling period information (e.g., first sampling period information T1) of the reference data (e.g., first sensor data 610) previously stored in the memory 330. According to an embodiment, the electronic device 300 may calculate the required time between the synchronization markers (e.g., first synchronization marker m1 and second synchronization marker m2) by multiplying the number of sampling data included between the synchronization markers (e.g., first synchronization marker m1 and second synchronization marker m2) by the sampling period information of the reference data (e.g., first sensor data 610) based on the positions of the synchronization markers included in the reference data (e.g., first sensor data 610). According to an embodiment, when the sensor data (e.g., third sensor data) directly generated by the electronic device 300 is selected as the reference data, the electronic device 300 may obtain a required time based on a time point of generation or transmission of a synchronization signal corresponding to each synchronization marker (e.g., first synchronization marker m1 and second synchronization marker m2). Referring to part (c) of FIG. 6B, the identification code may be the required time t2 between the synchronization markers (e.g., first synchronization marker m21 and second synchronization marker m22) of the second sensor data 620, and the identification code may be the required time t3 between the synchronization markers (e.g., first synchronization marker m31 and second synchronization marker m32) of the third sensor data 630. Referring to part (c) of FIG. 6B, the actual sampling period of the second sensor data 620 and/or the actual sampling period of the third sensor data 630 may be different from the second sampling period information T2 and/or the third sampling period information T3 stored in the electronic device 300, respectively, due to an error rate. When the second sensor data 620 is selected as the reference data, the electronic device 300 may set the required time t2 calculated by multiplying the number of sampling data included between the synchronization markers (e.g., first synchronization marker m21 and second synchronization marker m22) of the second sensor data 620 by the sampling period information of the second sensor data 620 as a reference, or when the third sensor data 630 is selected as the reference data, the electronic device 300 may set the required time t3 calculated by multiplying the number of sampling data included between the synchronization markers (e.g., first synchronization marker m31 and second synchronization marker m32) of the third sensor data 630 by the sampling period information of the third sensor data 630 as a reference.

Referring to part (d) of FIG. 6B, the electronic device 300 may correct the sampling period information and store the corrected sampling period information. According to various embodiments, the electronic device 300 may correct sampling period information (e.g., second sampling period information T2 and third sampling period information T3) of sensor data (e.g., second sensor data 620 and third sensor data 630) other than the reference data based on the sampling period information (e.g., first sampling period information T1) of the reference data (e.g., first sensor data 610). According to various embodiments, the electronic device 300 may correct the sampling period information (e.g., second sampling period information T2 and third sampling period information T3) of the sensor data (e.g., second sensor data 620 and third sensor data 630) other than the reference data based on the calculated required time tm and the synchronization marker positions of the sensor data other than the reference data. According to an embodiment, even in the case of different sensor data, the time at which the synchronization marker is generated may be considered to be substantially the same. That is, it can be seen that the synchronization markers including the same ID are generated at substantially the same time. Therefore, it can be considered that the physical required time between synchronization markers is substantially the same even between different sensor data. However, due to the error rate of the sampling period of the sensor, sampling may be performed with respect to each sensor data (e.g., first sensor data 610, second sensor data 620, and third sensor data 630) at a period different from the sampling period information (e.g., second sampling period information T2) stored in the memory 330. Accordingly, it is possible to set the sampling period information (e.g., first sampling period information T1) of the reference data (e.g., first sensor data 610) stored in the memory 330 as a true value, and correct the sampling period information (e.g., second sampling period information T2 and third sampling period information T3) of the sensor data (e.g., second sensor data 620 and third sensor data 630) other than the reference data. According to various embodiments, the electronic device 300 may correct sampling period information (e.g., second sampling period information T2 and third sampling period information T3) of the sensor data other than the reference data based on the calculated required time and the number of pieces of sample data between the synchronization markers of the sensor data (e.g., second sensor data 620 and third sensor data 630) other than the reference data. According to an embodiment, the electronic device 300 may determine that the required time tm calculated using the reference data (e.g., first sensor data 610) is the same as the required time between synchronization markers (e.g., first synchronization marker m1 and second synchronization marker m2) of sensor data (e.g., second sensor data 620 and third sensor data 630) other than the reference data. Accordingly, when the number of pieces of sample data between synchronization markers is divided with respect to the calculated required time tm, corrected sampling period information may be obtained. According to an embodiment, the electronic device 300 may check the number of pieces of sample data between the detected synchronization markers (e.g., between first synchronization marker m21 and second synchronization marker m22, and between first synchronization marker m31 and second synchronization marker m32) with respect to the remaining sensor data (e.g., second sensor data 620 and third sensor data 630) other than the reference data, and obtain corrected sampling period information (e.g., corrected second sampling period information T2' and corrected third sampling period information T3') based on the checked number of pieces of sample data. According to various embodiments, the electronic device 300 may store the corrected sampling period information (e.g., corrected second sampling period information T2' and corrected third sampling period information T3') in the memory 330. According to an embodiment, the electronic device 300 may update the pre-stored sampling period information (e.g., second sampling period information T2 and third sampling period information T3) with the corrected sampling period information (e.g., corrected second sampling period information T2' and corrected third sampling period information T3') and store the corrected sampling period information in the memory 330. According to an embodiment, the electronic device 300 may perform synchronization between the plurality of sensor data (e.g., first sensor data 610, second sensor data 620, and third sensor data 630) using the corrected sampling period information (e.g., corrected second sampling period information T2' and corrected third sampling period information T3'), and may analyze each sensor data (e.g., first sensor data 610, second sensor data 620, and third sensor data 630).

An electronic device according to various embodiments disclosed in the disclosure may include a communication module for communicatively establishing a connection with a first sensor device and a second sensor device, a memory for storing first sampling information including at least one of information on a sampling period and information on a sampling frequency of the first sensor device and second sampling information including at least one of information on a sampling period and information on a sampling frequency of the second sensor device, and a processor operatively connected to the communication module and the memory, wherein the processor is configured to transmit a synchronization signal for generating a synchronization marker to the first sensor device and the second sensor device according to a predetermined time interval, receive and store first sensor data including the synchronization marker from the first sensor device, receive and store second sensor data including the synchronization marker from the second sensor device, select reference data serving as a reference from among the first sensor data and the second sensor data, detect the synchronization marker from the first sensor data and the second sensor data, calculate a required time between the synchronization markers of the reference data based on the stored sampling information of the reference data and the position of the synchronization marker included in the detected reference data, and correct and store sampling information of the remaining sensor data other than the reference data based on the required time and the synchronization marker positions of the remaining sensor data other than the reference data.

In addition, the processor may continuously transmit the synchronization signal to the first sensor device and the second sensor device according to a predetermined period.

In addition, the synchronization signal may include a signal that causes the first sensor device to configure the synchronization mark on data sampled immediately before receiving the synchronization signal among the first sensor data, and a signal that causes the second sensor device to configure the synchronization mark on data sampled immediately before receiving the synchronization signal among the second sensor data.

In addition, the synchronization signal may include a signal that causes the first sensor device to configure the synchronization mark on data sampled immediately after receiving the synchronization signal among the first sensor data, and a signal that causes the second sensor device to configure the synchronization mark on data sampled immediately after receiving the synchronization signal among the second sensor data.

In addition, the synchronization signal may include an identifiable ID (identification), and the received synchronization marker may include the ID.

In addition, the ID may be configured corresponding to the transmission time of the synchronization signal.

In addition, the processor may detect the synchronization marker based on the ID included in the synchronization marker.

In addition, the processor may align the first sensor data and the second sensor data based on a position of a synchronization marker of reference data among the detected synchronization markers.

In addition, the processor may select reference data based on error rate information of at least one of a sampling period or a sampling frequency of each of the first sensor device and the second sensor device.

In addition, the processor may calculate required time between the synchronization markers based on pre-stored sampling information corresponding to the reference data among the first sampling information and the second sampling information, and the number of pieces of sample data between the synchronization markers of the reference data.

In addition, the processor may correct and store sampling information of the remaining sensor data other than the reference data based on the calculated required time and the number of pieces of sample data of the remaining sensor data other than the reference data.

In addition, the electronic device may further include a sensor module for generating third sensor data including sample data collected according to a predetermined third sampling period, wherein the memory may store in advance third sampling information including at least one of information on a sampling period of the sensor module and information on a sampling frequency, and the processor may generate and store a synchronization marker in the third sensor data at the same time as the synchronization signal transmission, detect the synchronization marker from the first sensor data, the second sensor data and the third sensor data, align the first sensor data, the second sensor data, and the third sensor data based on a position of the detected synchronization marker of the third sensor data, calculate a required time between the synchronization marker of the third sensor data based on the sampling information of the third sensor data and a position of the synchronization marker included in the third sensor data, and correct and store sampling information of the first sensor data and the second sensor data based on the required time and the synchronization marker positions of the first sensor data and the second sensor data.

A method of correcting sampling information of sensor data received from a plurality of sensor devices by an electronic device according to various embodiments of the disclosure may include simultaneously transmitting a synchronization signal for generating a synchronization marker to the first sensor device and the second sensor device connected to the electronic device at least two times based on a predetermined time interval, receiving and storing first sensor data including the synchronization marker from the first sensor device, receiving and storing second sensor data including the synchronization marker from the second sensor device, selecting reference data serving as a reference from among the first sensor data and the second sensor data, detecting the synchronization marker from the first sensor data and the second sensor data, calculating a required time between the synchronization markers of the reference data based on the sampling information of the reference data and the positions of the synchronization markers included in the detected reference data, and correcting and storing sampling information of the remaining sensor data other than the reference data based on the required time and the position of the synchronization marker of the remaining sensor data other than the reference data.

In addition, the transmitting of the synchronization signal may include continuously transmitting the synchronization signal to the first sensor device and the second sensor device according to a predetermined period.

In addition, the synchronization signal may include a signal that causes the first sensor device to configure the synchronization marker to data sampled immediately before receiving the synchronization signal among the first sensor data, and include a signal that causes the second sensor device to configure the synchronization marker to data sampled immediately before receiving the synchronization signal among the second sensor data.

In addition, the synchronization signal may include an identifiable ID (identification), the received synchronization marker may include the ID, and the processor may include detecting the synchronization marker based on the ID included in the synchronization marker.

In addition, the selecting reference data may include selecting the reference data based on error rate information of at least one of a sampling period or a sampling frequency of each of the first sensor device and the second sensor device.

In addition, the calculating a required time between the synchronization markers may include calculating the required time between the synchronization markers based on pre-stored sampling information corresponding to the reference data among the first sampling information and the second sampling information and the number of pieces of sample data between the synchronization markers of the reference data.

In addition, the correcting and storing sampling information may include correcting and storing sampling information of the remaining sensor data other than the reference data based on the calculated required time and the number of pieces of sample data of the remaining sensor data other than the reference data.

In addition, the method of correcting sampling information of sensor data received from a plurality of sensor devices by an electronic device may include generating third sensor data including sample data collected according to a predetermined third sampling period, generating and storing a synchronization marker in the third sensor data simultaneously with the transmission of the synchronization signal, detecting the synchronization marker from the first sensor data, the second sensor data, and the third sensor data, aligning the first sensor data, the second sensor data, and the third sensor data based on the position of the detected synchronization marker of the third sensor data, calculating a required time between the synchronization markers of the third sensor data based on the sampling information of the third sensor data and the positions of the synchronization markers included in the third sensor data, and correcting and storing sampling information of the first sensor data and the second sensor data based on the required time and the positions of the synchronization markers of the first sensor data and the second sensor data.

The electronic device according to various embodiments may be one of various types of electronic devices. The electronic devices may include, for example, a portable communication device (e.g., a smartphone), a computer device, a portable multimedia device, a portable medical device, a camera, a wearable device, or a home appliance. According to an embodiment of the disclosure, the electronic devices are not limited to those described above.

It should be appreciated that various embodiments of the disclosure and the terms used therein are not intended to limit the technological features set forth herein to particular embodiments and include various changes, equivalents, or replacements for a corresponding embodiment. With regard to the description of the drawings, similar reference numerals may be used to refer to similar or related elements. It is to be understood that a singular form of a noun corresponding to an item may include one or more of the things, unless the relevant context clearly indicates otherwise. As used herein, each of such phrases as "A or B," "at least one of A and B," "at least one of A or B," "A, B, or C," "at least one of A, B, and C," and "at least one of A, B, or C," may include any one of, or all possible combinations of the items enumerated together in a corresponding one of the phrases. As used herein, such terms as "1st" and "2nd," or "first" and "second" may be used to simply distinguish a corresponding component from another, and does not limit the components in other aspect (e.g., importance or order). It is to be understood that if an element (e.g., a first element) is referred to, with or without the term "operatively" or "communicatively," as "coupled with," "coupled to," "connected with," or "connected to" another element (e.g., a second element), it means that the element may be coupled with the other element directly (e.g., wiredly), wirelessly, or via a third element.

As used in connection with various embodiments of the disclosure, the term "module" may include a unit implemented in hardware, software, or firmware, and may interchangeably be used with other terms, for example, "logic," "logic block," "part," or "circuitry." A module may be a single integral component, or a minimum unit or part thereof, adapted to perform one or more functions. For example, according to an embodiment, the module may be implemented in a form of an application-specific integrated circuit (ASIC).

Various embodiments as set forth herein may be implemented as software (e.g., the program 140) including one or more instructions that are stored in a storage medium (e.g., internal memory 136 or external memory 138) that is readable by a machine (e.g., the electronic device 101). For example, a processor (e.g., the processor 120) of the machine (e.g., the electronic device 101) may invoke at least one of the one or more instructions stored in the storage medium, and execute it, with or without using one or more other components under the control of the processor. This allows the machine to be operated to perform at least one function according to the at least one instruction invoked. The one or more instructions may include a code generated by a complier or a code executable by an interpreter. The machine-readable storage medium may be provided in the form of a non-transitory storage medium. The term "non-transitory" simply means that the storage medium is a tangible device, and does not include a signal (e.g., an electromagnetic wave), but this term does not differentiate between where data is semi-permanently stored in the storage medium and where the data is temporarily stored in the storage medium.

According to an embodiment, a method according to various embodiments of the disclosure may be included and provided in a computer program product. The computer program product may be traded as a product between a seller and a buyer. The computer program product may be distributed in the form of a machine-readable storage medium (e.g., compact disc read only memory (CD-ROM)), or be distributed (e.g., downloaded or uploaded) online via an application store (e.g., PlayStore™), or between two user devices (e.g., smart phones) directly. If distributed online, at least part of the computer program product may be temporarily generated or at least temporarily stored in the machine-readable storage medium, such as memory of the manufacturer's server, a server of the application store, or a relay server.

According to various embodiments, each component (e.g., a module or a program) of the above-described components may include a single entity or multiple entities, and some of the multiple entities may be separately disposed in different components. According to various embodiments, one or more of the above-described components may be omitted, or one or more other components may be added. Alternatively or additionally, a plurality of components (e.g., modules or programs) may be integrated into a single component. In such a case, according to various embodiments, the integrated component may still perform one or more functions of each of the plurality of components in the same or similar manner as they are performed by a corresponding one of the plurality of components before the integration. According to various embodiments, operations performed by the module, the program, or another component may be carried out sequentially, in parallel, repeatedly, or heuristically, or one or more of the operations may be executed in a different order or omitted, or one or more other operations may be added.

While the disclosure has been shown and described with reference to various embodiments thereof, it will be understood by those skilled in the art that various changes in form and details may be made therein without departing from the spirit and scope of the disclosure as defined by the appended claims and their equivalents.

The invention claimed is:

1. An electronic device comprising:
    a communicator configured to communicatively establish a connection with a first sensor device and a second sensor device;
    a memory storing first sampling information and second sampling information, the first sampling information comprising at least one of information on a sampling period or information on a sampling frequency of the first sensor device, the second sampling information comprising at least one of information on a sampling period or information on a sampling frequency of the second sensor device; and
    a processor operatively connected to the communicator and the memory, the processor being configured to:
        transmit a synchronization signal for generating a synchronization marker to the first sensor device and the second sensor device based on a predetermined time interval,
        receive and store first sensor data comprising the synchronization marker received from the first sensor device,
        receive and store second sensor data comprising the synchronization marker received from the second sensor device,
        select reference data from among the first sensor data and the second sensor data, the reference data serving as a reference,
        detect the synchronization marker from the first sensor data and the second sensor data,
        calculate a required time between synchronization markers of the reference data based on sampling information of the reference data stored in the memory and positions of the synchronization markers of the reference data, and
        correct and store sampling information of remaining sensor data other than the reference data based on the required time and the positions of the synchronization markers of the remaining sensor data other than the reference data.

2. The electronic device of claim 1, wherein the processor is further configured to continuously transmit the synchronization signal to the first sensor device and the second sensor device according to a predetermined period.

3. The electronic device of claim 1, wherein the synchronization signal comprises:

a signal causing the first sensor device to configure the synchronization marker on data sampled immediately before receiving the synchronization signal among the first sensor data, and a signal causing the second sensor device to configure the synchronization marker on data sampled immediately before receiving the synchronization signal among the second sensor data.

4. The electronic device of claim 1, wherein the synchronization signal comprises:
a signal causing the first sensor device to configure the synchronization marker on data sampled immediately after receiving the synchronization signal among the first sensor data, and
a signal causing the second sensor device to configure the synchronization marker on data sampled immediately after receiving the synchronization signal among the second sensor data.

5. The electronic device of claim 1,
wherein the synchronization signal comprises an identifiable identification (ID), and
wherein the synchronization marker comprises the ID.

6. The electronic device of claim 5, wherein the ID corresponds to a transmission time of the synchronization signal.

7. The electronic device of claim 5, wherein the processor is further configured to detect the synchronization marker based on the ID included in the synchronization marker.

8. The electronic device of claim 1, wherein the processor is further configured to align the first sensor data and the second sensor data based on a position of a synchronization marker of the reference data among the synchronization markers.

9. The electronic device of claim 1, wherein the processor is further configured to select the reference data based on error rate information of at least one of the sampling period or the sampling frequency of each of the first sensor device and the second sensor device.

10. The electronic device of claim 1, wherein the processor is further configured to calculate required time between the synchronization markers based on pre-stored sampling information corresponding to the reference data among the first sampling information and the second sampling information, and a number of pieces of sample data between the synchronization markers of the reference data.

11. The electronic device of claim 1, wherein the processor is further configured to correct and store the sampling information of the remaining sensor data other than the reference data based on the calculated required time and a number of pieces of sample data of the remaining sensor data other than the reference data.

12. The electronic device of claim 1, further comprising:
a sensor configured to generate third sensor data comprising sample data collected based on a predetermined sampling period,
wherein the memory further stores in advance third sampling information comprising at least one of information on a sampling period of the sensor or information on a sampling frequency, and
wherein the processor is further configured to:
generate and store a synchronization marker in the third sensor data at a same time as the transmitting of the synchronization signal,
detect the synchronization marker from the first sensor data, the second sensor data, and the third sensor data,
align the first sensor data, the second sensor data, and the third sensor data based on a position of the synchronization marker of the third sensor data,
calculate a required time between the synchronization marker of the third sensor data based on the sampling information of the third sensor data and the position of the synchronization marker of the third sensor data, and
correct and store sampling information of the first sensor data and the second sensor data based on the required time and positions of the synchronization markers of the first sensor data and the second sensor data.

13. The electronic device of claim 1, wherein the synchronization marker comprises data confirming an arrival time of the synchronization signal.

14. The electronic device of claim 1, wherein the synchronization marker comprises data identifying sample data sampled at a specific point in time.

15. The electronic device of claim 1, wherein the reference data comprises data to be the reference for synchronization among a plurality of sensor data received from a plurality of sensor devices, respectively.

16. The electronic device of claim 1, wherein the selecting of the reference data comprises comparing a sampling period error rate of the first sensor device and the second sensor device to a sampling period error rate of the electronic device and selecting the reference data based on a result of the comparing.

17. The electronic device of claim 16, wherein the selecting of the reference data further comprises selecting sensor data of an external electronic device having a lowest sampling period error rate as the reference data.

18. A method of an electronic device correcting sampling information of sensor data received from a plurality of sensor devices, the method comprising:
simultaneously transmitting a synchronization signal for generating a synchronization marker to a first sensor device and a second sensor device connected to the electronic device based on a predetermined time interval;
receiving and storing first sensor data including the synchronization marker from the first sensor device;
receiving and storing second sensor data including the synchronization marker from the second sensor device;
selecting reference data from among the first sensor data and the second sensor data, the reference data serving as a reference;
detecting the synchronization marker from the first sensor data and the second sensor data;
calculating a required time between synchronization markers of the reference data based on sampling information of the reference data and positions of the synchronization markers of the reference data; and
correcting and storing sampling information of remaining sensor data other than the reference data based on the required time and a position of a synchronization marker of the remaining sensor data other than the reference data.

19. The method of claim 18, wherein the transmitting of the synchronization signal comprises continuously transmitting the synchronization signal to the first sensor device and the second sensor device based on a predetermined period.

20. The method of claim 18,
wherein the synchronization signal comprises a signal causing the first sensor device to configure the synchronization marker to data sampled immediately before receiving the synchronization signal among the first sensor data, and wherein the synchronization signal further comprises a signal causing the second sensor device to configure the synchronization marker to data sampled immediately before receiving the synchronization signal among the second sensor data.

* * * * *